United States Patent
Wigzell et al.

Patent Number: 5,958,410
Date of Patent: Sep. 28, 1999

[54] THERAPY OF SARCOIDOSIS

[75] Inventors: Hans Wigzell, Hagersten; Johan Grünewald; Carl Harald Janson, both of Stockholm, all of Sweden; Nancy Jones, Wayland, Mass.

[73] Assignee: Avant Immunotherapeutics, Inc., Needham, Mass.

[21] Appl. No.: 08/454,236

[22] PCT Filed: Dec. 14, 1992

[86] PCT No.: PCT/US92/10779

§ 371 Date: Nov. 6, 1995

§ 102(e) Date: Nov. 6, 1995

[87] PCT Pub. No.: WO94/14067

PCT Pub. Date: Jun. 23, 1994

[51] Int. Cl.[6] .......................... A61K 39/395; C07K 16/28
[52] U.S. Cl. .................... 424/144.1; 424/154.1; 424/179.1; 530/388.75; 530/391.7
[58] Field of Search .............. 424/144.1, 154.1, 424/179.1; 530/388.75, 391.7; 435/70.21, 346

[56] References Cited

PUBLICATIONS

Janson, C. H. et al. Cancer Immunol. Immunother. 28:225–232, 1989.
Hafler, D. et al. Immunology Today 17: 152–159, Apr. 1996.
Bell, J. et al., Eds, T Cell Receptors, Oxford University Press, Oxford, pp. 123–132, 1995.
Borgato, L. et al. Clin. Exp. Rheum. 15: 475–479, 1997.
Richert, J. R. et al. Neurology 45: 1919–1922, Oct. 1995.
Keegan et al., "Determination Of The Fine Specificity Of A Monoclonal Antibody (mab) To A Human T Cell Receptor (TCR) V Region", FASEB J 5(4), 1991, A615.
Grunewald, J. et al. Eur. J. Immunol. 22(1): 129–135, Jan. 1992.
Olsnes, S. et al. Immunol. Today 10: 291–295, Oct. 1989.
Urban, J. L. et al. Cell 54: 577–592, Oct. 1988.
Harris, W et al. TIBTECH 11: 42–44, Feb. 1993.
Seaver, S. Genetic Engineering News 14: 16 and 21, Aug. 1994.
Tisch, R. Proc. Natl. Acad. Sci. USA 91: 437–438, Jan. 1994.

*Primary Examiner*—Christina Y. Chan
*Assistant Examiner*—Evelyn Rabin
*Attorney, Agent, or Firm*—Pennie & Edmonds LLP

[57] ABSTRACT

Sarcoidosis is associated with $CD4^+$ T lymphocytes which express the T cell receptor $V_\alpha 2.3$ chain. Thus, a method for diagnosing sarcoidosis is provided which comprises contacting cells of a subject with a first monoclonal antibody, or an antigen-binding fragment or derivative, specific for an epitope of the variable region of the T cell receptor $V_\alpha 2.3$ chain and detecting the binding of the antibody. Also provided is a method for treating sarcoidosis in which a monoclonal antibody, or an antigen-binding fragment or derivative thereof, specific for an epitope of the variable region of the T cell receptor $V_\alpha 2.3$ chain is administered. Sarcoidosis is also treated by administering a therapeutically effective amount of a protein or a peptide comprising an amino acid sequence of the variable region of the T cell receptor $V_\alpha 2.3$ chain, or a functional derivative of the protein or peptide, or an antisense oligonucleotide which is complementary to the T cell receptor $V_\alpha 2.3$ mRNA.

3 Claims, 6 Drawing Sheets

```
ATG ATG ATA TCC TTG AGA GTT TTA CTG GTG ATC CTG TGG CTT CAG TTA    48

AGC TGG GTT TGG AGC CAA CGG AAG GAG GTG GAG CAG GAT CCT GGA CCC    96

TTC AAT GTT CCA GAG GGA GCC ACT GTC GCT TTC AAC TGT ACT TAC AGC   144

AAC AGT GCT TCT CAG TCT TTC TTC TGG TAC AGA CAG GAT TGC AGG AAA   192

GAA CCT AAG TTG CTG ATG TCC GTA TAC TCC AGT GGT AAT GAA GAT GGA   240

AGG TTT ACA GCA CAG CTC AAT AGA GCC AGC CAG TAT ATT TCC CTG CTC   288

ATC AGA GAC TCC AAG CTC AGT GAT TCA GCC ACC TAC CTC TGT GTG GTG   336

AAC ATT CGC CCA GGA AAC ACA CCT CTT GTC TTT GGA AAG GGC ACA AGA   384

CTT TCT GTG ATT CCA AAT ATC C                                     406
```

FIG. 4

[Leader...
Met Met Ile Ser Leu Arg Val Leu Leu Val Ile Leu Trp Leu Gln Leu
1               5                   10                  15

...Leader] [V region...
Ser Trp Val Trp Ser Gln Arg Lys Glu Val Gln Asp Pro Gly Pro
            20                  25                  30

Phe Asn Val Pro Glu Gly Ala Thr Val Ala Phe Asn Cys Thr Tyr Ser
                35                  40                  45

Asn Ser Ala Ser Gln Ser Phe Phe Trp Tyr Arg Gln Asp Cys Arg Lys
            50                  55                  60

Glu Pro Lys Leu Leu Met Ser Val Tyr Ser Ser Gly Asn Glu Asp Gly
65                  70                  75                  80

FIG. 5A

Arg Phe Thr Ala Gln Leu Asn Arg Ala Ser Gln Tyr Ile Ser Leu Leu
                    85                  90                  95

Ile Arg Asp Ser Lys Leu Ser Asp Ser Ala Thr Tyr Leu Cys Val Val
                    100                 105                 110

.V] [J region...
Asn Ile Arg Pro Gly Asn Thr Pro Leu Val Phe Gly Lys Gly Thr Arg
                    115                 120                 125

Leu Ser Val Ile Pro Asn Ile
                    130                 135

FIG. 5B

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 406 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 1..406

(xi) SEQUENCE DESCRIPTION: SEQ ID NO:1:

```
ATG ATG ATA TCC TTG AGA GTT TTA CTG GTG ATC CTG TGG CTT CAG TTA      48
Met Met Ile Ser Leu Arg Val Leu Leu Val Ile Leu Trp Leu Gln Leu
  1               5                  10                  15

AGC TGG GTT TGG AGC CAA CGG AAG GAG GTG GAG CAG GAT CCT GGA CCC      96
Ser Trp Val Trp Ser Gln Arg Lys Glu Val Glu Gln Asp Pro Gly Pro
             20                  25                  30

TTC AAT GTT CCA GAG GGA GCC ACT GTC GCT TTC AAC TGT ACT TAC AGC     144
Phe Asn Val Pro Glu Gly Ala Thr Val Ala Phe Asn Cys Thr Tyr Ser
         35                  40                  45

AAC AGT GCT TCT CAG TCT TTC TTC TGG TAC AGA CAG GAT TGC AGG AAA     192
Asn Ser Ala Ser Gln Ser Phe Phe Trp Tyr Arg Gln Asp Cys Arg Lys
     50                  55                  60

GAA CCT AAG TTG CTG ATG TCC GTA TAC TCC AGT GGT AAT GAA GAT GGA     240
Glu Pro Lys Leu Leu Met Ser Val Tyr Ser Ser Gly Asn Glu Asp Gly
 65                  70                  75                  80

AGG TTT ACA GCA CAG CTC AAT AGA GCC AGC CAG TAT ATT TCC CTG CTC     288
Arg Phe Thr Ala Gln Leu Asn Arg Ala Ser Gln Tyr Ile Ser Leu Leu
                 85                  90                  95

ATC AGA GAC TCC AAG CTC AGT GAT TCA GCC ACC TAC CTC TGT GTG GTG     336
Ile Arg Asp Ser Lys Leu Ser Asp Ser Ala Thr Tyr Leu Cys Val Val
                100                 105                 110

AAC ATT CGC CCA GGA AAC ACA CCT CTT GTC TTT GGA AAG GGC ACA AGA     384
Asn Ile Arg Pro Gly Asn Thr Pro Leu Val Phe Gly Lys Gly Thr Arg
            115                 120                 125

CTT TCT GTG ATT CCA AAT ATC C                                       406
Leu Ser Val Ile Pro Asn Ile
        130                 135
```

(2) INFORMATION FOR SEQ ID NO:2:

(i) SEQUENCE CHARACTERISTICS:
      (A) LENGTH: 135 amino acids
      (B) TYPE: amino acid
      (D) TOPOLOGY: linear (ii) MOLECULE TYPE: protein (xi) SEQUENCE DESCRIPTION: SEQ ID NO:2:

Met Met Ile Ser Leu Arg Val Leu Leu Val Ile Leu Trp Leu Gln Leu
1               5                   10                  15

Ser Trp Val Trp Ser Gln Arg Lys Glu Val Glu Gln Asp Pro Gly Pro
            20                  25                  30

Phe Asn Val Pro Glu Gly Ala Thr Val Ala Phe Asn Cys Thr Tyr Ser
            35                  40                  45

Asn Ser Ala Ser Gln Ser Phe Phe Trp Tyr Arg Gln Asp Cys Arg Lys
        50                  55                  60

Glu Pro Lys Leu Leu Met Ser Val Tyr Ser Ser Gly Asn Glu Asp Gly
65                  70                  75                  80

Arg Phe Thr Ala Gln Leu Asn Arg Ala Ser Gln Tyr Ile Ser Leu Leu
                85                  90                  95

Ile Arg Asp Ser Lys Leu Ser Asp Ser Ala Thr Tyr Leu Cys Val Val
                100                 105                 110

Asn Ile Arg Pro Gly Asn Thr Pro Leu Val Phe Gly Lys Gly Thr Arg
            115                 120                 125

Leu Ser Val Ile Pro Asn Ile
130                 135

(2) INFORMATION FOR SEQ ID NO:3:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1...112
        (D) OTHER INFORMATION: /label= Name
            /note= "Corresponding to VJ region of SEQ ID NO:2"

(xi) SEQUENCE DESCRIPTION: SEQ ID NO:3:

Lys Glu Val Glu Gln Asp Pro Gly Pro Phe Asn Val Pro Glu Gly Ala
1               5                   10                  15

Thr Val Ala Phe Asn Cys Thr Tyr Ser Asn Ser Ala Ser Gln Ser Phe
            20                  25                  30

Phe Trp Tyr Arg Gln Asp Cys Arg Lys Glu Pro Lys Leu Leu Met Ser
            35                  40                  45

Val Tyr Ser Ser Gly Asn Glu Asp Gly Arg Phe Thr Ala Gln Leu Asn
        50                  55                  60

Arg Ala Ser Gln Tyr Ile Ser Leu Leu Ile Arg Asp Ser Lys Leu Ser
65                  70                  75                  80

Asp Ser Ala Thr Tyr Leu Cys Val Val Asn Ile Arg Pro Gly Asn Thr
                85                  90                  95

Pro Leu Val Phe Gly Lys Gly Thr Arg Leu Ser Val Ile Pro Asn Ile
                100                 105                 110

(2) INFORMATION FOR SEQ ID NO:4:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: peptide

```
        (ix) FEATURE:
              (A) NAME/KEY: Peptide
              (B) LOCATION: 1..90
              (D) OTHER INFORMATION: /label= Name
                   /note= "Corresponding to V region of SEQ ID NO:2"

(xi) SEQUENCE DESCRIPTION: SEQ ID NO:4:

Lys Glu Val Glu Gln Asp Pro Gly Pro Phe Asn Val Pro Glu Gly Ala
1               5                  10                  15

Thr Val Ala Phe Asn Cys Thr Tyr Ser Asn Ser Ala Ser Gln Ser Phe
             20                  25                  30

Phe Trp Tyr Arg Gln Asp Cys Arg Lys Glu Pro Lys Leu Leu Met Ser
         35                  40                  45

Val Tyr Ser Ser Gly Asn Glu Asp Gly Arg Phe Thr Ala Gln Leu Asn
     50                  55                  60

Arg Ala Ser Gln Tyr Ile Ser Leu Leu Ile Arg Asp Ser Lys Leu Ser
65                  70                  75                  80

Asp Ser Ala Thr Tyr Leu Cys Val Val Asn
             85                  90

(2) INFORMATION FOR SEQ ID NO:5:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..22
         (D) OTHER INFORMATION: /note= "Corresponding to J region
             of SEQ ID 2"

(xi) SEQUENCE DESCRIPTION: SEQ ID NO:5:

Ile Arg Pro Gly Asn Thr Pro Leu Val Phe Gly Lys Gly Thr Arg Leu
1               5                  10                  15

Ser Val Ile Pro Asn Ile
             20

(2) INFORMATION FOR SEQ ID NO:6:

(i) SEQUENCE CHARACTERISTICS:
         (A) LENGTH: 34 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..34
         (D) OTHER INFORMATION: /note= "Corresponding to CDR1 of
             the TCR V 2.3 region"

(xi) SEQUENCE DESCRIPTION: SEQ ID NO:6:

Lys Glu Val Glu Gln Asp Pro Gly Pro Phe Asn Val Pro Glu Gly Ala
1               5                  10                  15

Thr Val Ala Phe Asn Cys Thr Tyr Ser Asn Ser Ala Ser Gln Ser Phe
             20                  25                  30

Phe Trp (2) INFORMATION FOR SEQ ID NO:7:
```

(i) SEQUENCE CHARACTERISTICS:
    (A) LENGTH: 47 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..47
    (D) OTHER INFORMATION: /note= "Corresponding to CDR2 of
        the TCR V 2.3 region."

(xi) SEQUENCE DESCRIPTION: SEQ ID NO:7:

Tyr Arg Gln Asp Cys Arg Lys Glu Pro Lys Leu Leu Met Ser Val Tyr
1               5                   10                  15

Ser Ser Gly Asn Glu Asp Gly Arg Phe Thr Ala Gln Leu Asn Arg Ala
            20                  25                  30

Ser Gln Tyr Ile Ser Leu Leu Ile Arg Asp Ser Lys Leu Ser Asp
        35                  40                  45

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1...31
        (D) OTHER INFORMATION: /note= "Corresponding to CDR3 of the
            TCR V 2.3 region"

(xi) SEQUENCE DESCRIPTION: SEQ ID NO:8:

Ser Ala Thr Tyr Leu Cys Val Val Asn Ile Arg Pro Gly Asn Thr Pro
1               5                   10                  15

Leu Val Phe Gly Lys Gly Thr Arg Leu Ser Val Ile Pro Asn Ile
            20                  25                  30

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..21
        (D) OTHER INFORMATION: /label= P1

(xi) SEQUENCE DESCRIPTION: SEQ ID NO:9:

Lys Glu Val Glu Gln Asp Pro Gly Pro Phe Asn Val Pro Glu Gly Ala
1               5                   10                  15

Thr Val Ala Phe Asn
            20

(2) INFORMATION FOR SEQ ID NO:10:

(i) SEQUENCE CHARACTERISTICS:
        (A) LENGTH: 17 amino acids (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..17
         (D) OTHER INFORMATION: /label= P2

(xi) SEQUENCE DESCRIPTION: SEQ ID NO:10:

Cys Thr Tyr Ser Asn Ser Ala Ser Gln Ser Phe Phe Trp Tyr Arg Gln
1               5                  10                  15

Asp (2) INFORMATION FOR SEQ ID NO:11:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..16
         (D) OTHER INFORMATION: /label= P3

(xi) SEQUENCE DESCRIPTION: SEQ ID NO:11:

Cys Arg Lys Glu Pro Lys Leu Leu Met Ser Val Tyr Ser Ser Gly Asn
1               5                  10                  15

(2) INFORMATION FOR SEQ ID NO:12:

(i) SEQUENCE CHARACTERISTICS:
         (A) LENGTH: 32 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..32
         (D) OTHER INFORMATION: /label= P4

(xi) SEQUENCE DESCRIPTION: SEQ ID NO:12:

Glu Asp Gly Arg Phe Thr Ala Gln Leu Asn Arg Ala Ser Gln Tyr Ile
1               5                  10                  15

Ser Leu Leu Ile Arg Asp Ser Lys Leu Ser Asp Ser Ala Thr Tyr Leu
            20                  25                  30

(2) INFORMATION FOR SEQ ID NO:13:

(i) SEQUENCE CHARACTERISTICS:
         (A) LENGTH: 26 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..26
         (D) OTHER INFORMATION: /label= P5

(xi) SEQUENCE DESCRIPTION: SEQ ID NO:13:

```
-continued

Cys Val Val Asn Ile Arg Pro Gly Asn Thr Pro Leu Val Phe Gly Lys
1               5                   10                  15

Gly Thr Arg Leu Ser Val Ile Pro Asn Ile
            20              25
```

THERAPY OF SARCOIDOSIS

1. INTRODUCTION

The present invention in the fields of immunology and medicine relates to methods for diagnosing and treating sarcoidosis based on the presence in the lungs of sarcoidosis patients of T lymphocytes expressing the $V_{60}$ 2.3 variant of the T cell receptor α chain. Monoclonal antibodies specific for an epitope of the variable region of the T cell receptor $V_{60}$ 2.3 chain, or epitope-binding fragments or derivatives of the antibody, are useful in diagnostic and therapeutic methods.

2. BACKGROUND OF THE INVENTION

2.1. Sarcoidosis

Sarcoidosis is a chronic inflammatory disorder with unknown etiology, characterized by non-caseating granulomas in affected organs, in particular, the lungs, lymph nodes, skin and eyes. The disorder is typically accompanied by nonspecific depression of cell-mediated as well as humoral immune responsiveness, and by polyclonal hypergammaglobulinemia (Siltzbach, L. E., *Amer. Rev. Resp. Dis.* 97:1–8 (1968); Roberts, C. R. et al., *Ann. Intern. Med.* 94:73 (1981)). At least 90% of the patients with this multisystem disease have pulmonary manifestations characterized by chronic inflammation, granuloma formation and some cases of pulmonary fibrosis. These processes affect the alveoli, airways and blood vessels resulting in an impairment of normal gas exchange. The inflammatory process precedes the other symptoms of sarcoidosis.

$CD4^+$ T helper (Th) cells are believed to play a central role in the pathogenesis of sarcoidosis. Such activated cells accumulate in the alveolar space, spontaneously release IL2 and proliferate at high rates in vitro and express HLA-DR, a marker of T cell activation (Hunninghake, G. et al., *N. Engl. J. Med.* 305:429 (1981)). The T cells in the lung which spontaneously release IL2 are primarily of the $CD4^+HLA-DR^+$ class (Saltini, C. et al., *J. Clin. Invest.* 77:1962–1970 (1986)). The release of cytokines results in modulation of granuloma formation and polyclonal activation of B cells to secrete immunoglobulin (Hunninghake et al., supra). A subset of Th cells identified by a mAb designated 5/9, which detects activated T cells, was shown to predominate in the lungs of sarcoidosis patients and was responsible for the release of lymphokines and the polyclonal B cell activation (Rossi, G. A. et al., *Am. Rev. Respir. Dis.* 133:1086–1090 (1986)). In sarcoidosis patients with high-intensity alveolitis, T lymphocytes from lung (but not those from peripheral blood) spontaneously release IL2 in vitro and replicate at a high rate (Pinkston, P. et al., *N. Engl. J. Med.* 308:793 (1983)).

2.2. The T Cell Antigen Receptor

T lymphocytes recognize and interact with antigens by means of a cell-surface molecular complex known as the T cell antigen receptor (TCR) complex. The TCR is a clone-specific heterodimeric protein on T cells, which recognizes its "target" antigen in association with a major histocompatibility complex (MHC)-encoded glycoprotein on the surface of antigen presenting cells (APC). $CD4^+$ T cells recognize predominantly antigen associated with MHC class II molecules whereas $CD8^+$ T cells recognize antigen associated with MHC class I molecules. The TCR is noncovalently associated with the CD3 complex of molecules. Approximately 90% of peripheral blood T cells express a TCR which is a heterodimer of an α and a β chain. A small percentage of T cells express a TCR consisting of a heterodimer comprising a γ and a δ polypeptide chain. (See, for example, Davis et al., 1988, *Nature* 334:395–402; Marrack et al., 1986, *Sci. Amer.* 254:36; Meuer et al., 1984, *Ann. Rev. Immunol.* 2:23–50; Brenner et al., 1986, *Nature* 322:145–159; Krangel et al., 1987, *Science* 237:1051–1055; Hata et al., 1987, *Science* 238:678–682; Hochstenbach et al., 1988, *J. Exp. Med.* 168:761–776).

In a given T cell or clone of T cells, each TCR chain is a unique combination of domains designated variable (V), [(diversity (D),] joining (J), and constant (C) (Siu et al., 1984, *Cell* 37:393; Yanagi et al., 1985, *Proc. Natl. Acad. Sci. USA* 82:3430). Hypervariable regions have also been identified (Patten et al., 1984, *Nature* 312:40; Becker et al., 1985, *Nature* 317:430). The V domains of the TCR α and β chains are created through rearrangement of each of 60 V and 75 J and of one each of 70 V, 2 D and 13 J gene segments, respectively (Ferradini, L. et al., *Eur. J. Immunol.* 21:935 (1991); Roman-Roman, S. et al., *Eur. J. Immunol.* 21:927 (1991)). Adding further junctional and N-linked diversity, and multiple reading frames for D segments, the calculated variability of the α/β TCR is in the order of $10^{15}$ (Davis, M. et al., *Nature* 334:395 (1988)). In each T cell clone, the combination of V, D and J domains of both the α and the β chains or of both the δ and γ chains participates in antigen recognition in a manner which is uniquely characteristic of that T cell clone and defines a unique "binding site," also known as the idiotype, of the T cell clone. In contrast, the TCR C domain does not participate in antigen binding.

2.3. T Cell Receptor Expression in Sarcoidosis

Certain diseases, in particular those with autoimmune etiologies, are associated with the increase in frequencies of T lymphocytes expressing a particular α or β TCR V region gene (Hafler, D. A. et al., *J. Exp. Med.* 167:1313 (1988); Mantegazza, R. et al., *Autoimmunity* 3:431 (1990)). Such limited or preferential usage of specific TCRs has recently been observed in sarcoidosis (Moller, D. et al., *J. Clin. Invest.* 82:1183 (1988); Balbi, B. et al., *J. Clin. Invest.* 85:1353 (1990); Tamura, N. et al., *J. Exp. Med.* 172:169 (1990)).

Moller et al., (supra) found that, in a subgroup of sarcoidosis patients, T cells obtained from lungs showed an increase in the percentage of $CD4^+$ cells expressing the TCR $V_\beta 8$ chain. In contrast, in the blood of the same patients, there was an increased prevalence of $V_{\beta 2} 8^+$ cells in the $CD^+$ T cell population. The authors concluded that a selective accumulation of T cells expressing a particular TCR β chain occurred in this disease.

Balbi et al., (supra) disclosed a marked elevation of $CD3^+TCR\gamma\delta^+$ T cells in the lungs and blood of sarcoidosis patients, with the majority of the $\gamma\delta^+$ T cells expressing a particular γ chain V region, $V_\gamma 9$.

Tamura et al., (supra) further analyzed TCR Vγ (and Vδ) chain usage in sarcoidosis patients by sequencing junctional (N) regions of the common human $V_\gamma 9$ gene segments. They disclosed a broad diversity of $V_\gamma 9$ junctional sequences in normals, but a striking over-representation of specific junctional region sequences in a subgroup of sarcoidosis patients. The authors speculated that this type of TCR usage represents a response to specific antigenic stimuli and that the γ/δ T cells might play a specific role in granuloma formation.

2.4. Antisense Oligonucleotides as Therapeutic Agents

Antisense oligonucleotides are thought to inhibit gene expression by blocking the processing and translation of the sense mRNA or by disrupting interactions with sequence-specific RNA binding proteins. For example, a plasmid having a promoter which directs transcription of RNA complementary to normal thymidine kinase (TK) mRNA substantially reduces expression of TK from a normal plasmid with which it is cotransfected into a cell (Izant et al., *Cell* 36:1007 (1984).

The constitutive expression of antisense RNA in cells can inhibit the expression of numerous genes in mammals and plants, and the list continually grows (Hambor, J. E. et al., *J. Exp. Med.* 168:1237–1245 (1988); Holt, J. T. et al., *Proc. Natl. Acad. Sci. USA* 83:4794–4798 (1986); Izant, J. G. et al., *Cell* 36:1007–1015 (1984); Izant, J. G., et al., *Science* 229:345–352 (1985); De Benedetti, A. et al., *Proc. Nat.. Acad. Sci.* 84:658–662 (1987)).

Antisense effects may be due to blockage of translation or prevention of splicing, both of which have been observed in vitro. Interference with splicing also allows the use of intron sequences (Munroe, S. H., *EMBO. J.* 7:2523–2532 (1988) which should be less conserved and therefore result in greater species specificity of inhibition.

Antisense technology has been applied successfully to primary human T lymphocytes to inhibit the replication of a virus, HTLV-I (Ruden et al., *J. Virol.* 63:677–682 (1989)) by engineering the cells to express an antisense RNA to parts of the viral genome. For example, antisense-encoding DNAs operably linked to the cytomegalovirus immediate early promoter expressed antisense RNA and exerted an inhibitory effect on cell proliferation.

3. SUMMARY OF THE INVENTION

The present invention relates to methods for diagnosing and treating sarcoidosis using a binding partner specific for the variable region of the TCR $V_{60}$ 2.3 chain, preferably antibodies specific for epitopes of the TCR $V_{60}$2.3 chain variable region. These approaches are based on the present inventors' discovery that a particular subset of $CD4^+$ lymphocytes which express a TCR recognized by an antibody specific for the TCR $V_\alpha$2.3 chain is preferentially compartmentalized in the lungs of sarcoidosis patients. In particular, levels of $V_\alpha$2.3-positive cells were increased among $CD4^+$ T cells in bronchoalveolar lavage (BAL) relative to $CD^+$ peripheral blood lymphocyte (PBL) populations.

Thus, the present invention is directed to a method for diagnosing sarcoidosis in a patient suspected of having sarcoidosis, comprising detecting an increase in the number of cells expressing a T cell antigen receptor $V_\alpha$2.3 chain in a sample from the patient, relative to the number of cells in a comparable sample obtained from a healthy subject or relative to the number in a baseline sample.

The present invention further provides a method for diagnosing sarcoidosis in a patient suspected of having sarcoidosis, comprising:

(a) determining the ratio of the number of cells expressing a T cell antigen receptor $V_\alpha$2.3 chain to the number of a second group of cells, such as total lymphocytes, total T cells or CD4-positive T cells, in a sample from the lungs or from bronchoalveolar lavage fluid obtained from the patient; and (b) comparing the ratio determined in step (a) with the ratio of the number of cells expressing a T cell receptor $V_\alpha$2.3 chain to the number of cells of the second group in a sample from the lungs or from bronchoalveolar lavage fluid obtained from a healthy subject, or in the blood of the patient or the healthy subject, or with a baseline sample ratio;

wherein an increased ratio of the number of cells expressing the $V_\alpha$2.3 chain in the lungs or bronchoalveolar lavage fluid of the patient indicates the presence of sarcoidosis.

Preferably, in the above method, the detecting is performed on cells in bronchoalveolar lavage fluid obtained from the patient, and the comparing is with the ratio of cells in the peripheral blood of the patient.

Preferably, the determining step above comprises:

(i) contacting cells of the patient with a first binding partner which binds specifically to the variable region of the T cell receptor $V_\alpha$2.3 chain; and (ii) detecting the specific binding of the binding partner to the cells.

The first binding partner above is preferably an antibody, most preferably a monoclonal antibody, specific for an epitope of the variable region of the T cell receptor $V_\alpha$2.3 chain, or an epitope-binding fragment or derivative of the antibody. A most preferred monoclonal antibody is has binding characteristics of F1, as produced by the hybridoma deposited with the ATCC and assigned accession number HB 11176.

Another embodiment of the above method further comprises, before, during or after step (a), determining the number of CD4-positive cells in the lungs or bronchoalveolar lavage fluid, such as by detecting the binding to the cells of a second binding partner specific for the CD4 molecule, preferably a second monoclonal antibody specific for an epitope of the CD4 molecule, or an epitope-binding fragment or derivative of the second antibody.

The contacting in the above methods may be in vitro or in vivo. The sample may be a histological specimen, such as lung tissue.

The present invention also provides a method for diagnosing sarcoidosis in a patient suspected of having sarcoidosis, comprising:

(a) determining the number of T lymphocytes expressing the variable region of the T cell receptor $V_\alpha$2.3 chain in a sample containing T lymphocytes from the lungs or bronchoalveolar lavage fluid of the patient;

(b) determining the number of CD4-positive T lymphocytes in the sample;

(c) determining the percentage of CD4-positive cells which express the variable region of the T cell receptor $V_\alpha$2.3 chain in the sample; and (d) comparing the percentage determined in step (c) with the percentage of CD4-positive cells which express the variable region of the T cell antigen receptor $V_\alpha$2.3 chain in a sample containing T lymphocytes from the lungs or bronchoalveolar lavage fluid of a healthy subject or from the peripheral blood of the patient or the healthy subject, or a baseline sample percentage, wherein an increased percentage of CD4-positive cells expressing the $V_\alpha$2.3 chain in the lungs or bronchoalveolar lavage fluid of the patient indicates the presence of sarcoidosis.

In the above method, (i) the number of T lymphocytes expressing the variable region of the T cell receptor $V_\alpha$2.3 chain is preferably determined by contacting the cells with a first monoclonal antibody specific for the variable region of the T cell receptor $V_\alpha$2.3 chain, or an epitope-binding fragment or derivative of the monoclonal antibody, and detecting the immunospecific binding of the first antibody, fragment or derivative to the T lymphocytes; and (ii) the number of CD4-positive T lymphocytes is preferably determined by contacting the cells with a second monoclonal antibody specific for the CD4 molecule, or an epitope-binding fragment or derivative of the second antibody, and detecting the binding of the second antibody, fragment or derivative to the T lymphocytes.

A preferred first monoclonal antibody has binding characteristics of F1, as produced by the hybridoma deposited with the ATCC and assigned accession number HB 11176.

Also provided is a method for diagnosing sarcoidosis in a subject suspected of having sarcoidosis, comprising detecting in a nucleic acid preparation derived from a T lymphocyte-containing sample from the subject the presence of rearranged nucleic acid sequence, mRNA or DNA, encoding the variable region of a T cell receptor $V_\alpha 2.3$ chain.

The present invention is also directed to methods for treating sarcoidosis in a subject. In a preferred embodiment, the method comprises administering to the subject a therapeutically effective amount of a binding partner of the T cell receptor $V_\alpha 2.3$ chain. A preferred binding partner is an antibody, preferably a monoclonal antibody specific for an epitope of the variable region of the T cell receptor $V_\alpha 2.3$ chain, or an epitope-binding fragment or derivative of the monoclonal antibody. A preferred monoclonal antibody has binding characteristics of F1, as produced by the hybridoma deposited with the ATCC and assigned accession number HB 11176. The binding partner, preferably an antibody, fragment, or derivative thereof, may be linked to a pharmacologic agent.

Also provided is a method of treating sarcoidosis in a subject, comprising administering to the subject a therapeutically effective amount of a protein or a peptide having at least about 15 amino acids comprising an amino acid sequence of the variable region of the T cell receptor $V_\alpha 2.3$ chain (FIG. 4). Preferably the protein or peptide is selected from the group consisting of peptides having the amino acid sequence:

(a) MMISLRVLLVIL-WLQLSWVVSQRKEVEQDPGPFNVPE-GATVAFNCTYSN SASQSFFWYRQDCRKEPKLLMS-VYSSGNEDGRFTAQLNRASQYISLLIR DSKLSDSATYLCVVNIRPGNTPLVF-GKGTRLSVIPNI (SEQ ID NO:2);
(b) KEVEQDPGPFNVPEGATVAFNCTYSN-SASQSFFWYRQDCRKEPKLLMSV YSSGNEDGR-FTAQLNRASQYISLLIRDSKLSDSATYL-CVVNIRPGNTPL VFGKGTRLSVIPNI (SEQ ID NO:3);
(c) KEVEQDPGPFNVPEGATVAFNCTYSN-SASQSFFWYRQDCRKEPKLLMSV YSSGNEDGR-FTAQLNRASQYISLLIRDSKLSDSATYLCVVN (SEQ ID NO:4);
(d) IRPGNTPLVFGKGTRLSVIPNI (SEQ ID NO:5);
(e) KEVEQDPGPFNVPEGATVAFNCTYSNSASQSFFW (SEQ ID NO:6);
(f) YRQDCRKEPKLLMSVYSSGNEDGR-FTAQLNRASQYISLLIRDSKLSD (SEQ ID NO:7); and
(g) SATYLCVVNIRPGNTPLVFGKGTRLSVIPNI (SEQ ID NO:8).

The peptide may preferably have between about 15 and 32 amino acids, and is preferably selected from the group consisting of the peptides having the amino acid sequence:

(a) KEVEQDPGPFNVPEGATVAFN (SEQ ID NO:9);
(b) CTYSNSASQSFFWYRQD (SEQ ID NO:10);
(c) CRKEPKLLMSVYSSGN (SEQ ID NO:11);
(d) EDGRFTAQLNRASQYISLLIRDSKLSDSATYL (SEQ ID NO:12); and
(e) CVVNIRPGNTPLVFGKGTRLSVIPNI (SEQ ID NO:13).

The above protein or peptide may be linked to a pharmacologic agent. Also provided are peptides or proteins comprising the foregoing sequences.

The present invention also includes a therapeutic composition useful for the treatment of sarcoidosis, comprising:

(a) an effective amount of a T cell receptor $V_\alpha 2.3$ chain protein or peptide, as above; and
(b) a suitable pharmaceutical carrier.

Another embodiment of a therapeutic composition useful for the treatment of sarcoidosis comprises:

(a) an effective amount of a monoclonal antibody specific for an epitope of the variable region of the T cell receptor $V_\alpha 2.3$ chain, or an antigen-binding fragment or derivative of the monoclonal antibody; and
(b) a suitable pharmaceutical carrier.
A preferred mAb is the F1 mAb Also provided is an isolated antisense oligonucleotide consisting of at least about fifteen nucleotides and comprising a sequence complementary to at least a portion of an RNA transcript of the human TCR $V_\alpha 2.3$ gene, which oligonucleotide is hybridizable to the RNA transcript and is capable of interfering with expression of the $V_\alpha 2.3$ gene. A pharmaceutical composition comprises the above oligonucleotide and a pharmaceutically acceptable carrier.

The present invention provides a composition comprising a therapeutically effective amount of a mAb specific for an epitope of the variable region of the T cell receptor $V_\alpha 2.3$ chain, preferably the F1 mAb, or an antigen-binding fragment or derivative of the mAb for use in treating sarcoidosis.

Also provided is the use of a composition comprising a therapeutically effective amount of a mAb specific for an epitope of the variable region of the T cell receptor $V_\alpha 2.3$ chain, preferably the F1 mAb, or an antigen-binding fragment or derivative of the mAb, for the manufacture of a medicament in the treatment of sarcoidosis.

In another embodiment is provided a composition comprising a therapeutically effective amount of a protein or a peptide having at least about 15 amino acids comprising an amino acid sequence of the variable region of the T cell receptor $V_\alpha 2.3$ chain for use in treating sarcoidosis.

Also provided is the use of a composition comprising a therapeutically effective amount of a protein or a peptide having at least about 15 amino acids comprising an amino acid sequence of the variable region of the T cell receptor $Va_{\alpha 2.3}$ chain for the manufacture of a medicament in the treatment of sarcoidosis.

4. DESCRIPTION OF THE FIGURES

FIG. 1 is a graph showing the percentage of $V_\alpha 2.3^+CD4^+$ T cells in PBL (□) and BAL (■) from 11 patients with sarcoidosis (panel A) and from four controls (panel B).

FIG. 2 is a flow cytometry profile from a double-staining experiment with lymphocyte gated BAL cells from patient no. 10. The ordinate represents cells stained with PE-conjugated (fluorescence two) anti-CD4. The abscissa represents cells detected by FITC-labeled (fluorescence one): (a) normal mouse serum (NMS) (b) $V_\alpha 2.3$, and (c) OKT3. The CD4$^+$ cells positively stained with the FITC-labelled mAb were (a) 0.2%, (b) 31.9% and (c) 99.8%.

FIG. 3 is a diagram showing percentage of $V_\alpha 2.3^+CD4^+$ cells in BAL(abscissa) and PBL (ordinate) in patient nos. 1

(x), 6 (■), 7 (●) and 10 (+) sampled for the first (a) and the second (b) analysis.

FIG. 4 shows the nucleotide sequence [SEQ ID NO:1] of the entire variable region of the TCR $V_\alpha 2.3$ gene, including the leader, V and J regions.

FIG. 5 shows the amino acid sequence [SEQ ID NO:2] of the entire variable region of the TCR $V_\alpha 2.3$ protein chain. The boundaries of the leader, V and J regions are shown.

5. DETAILED DESCRIPTION OF THE INVENTION

Figure 1B:
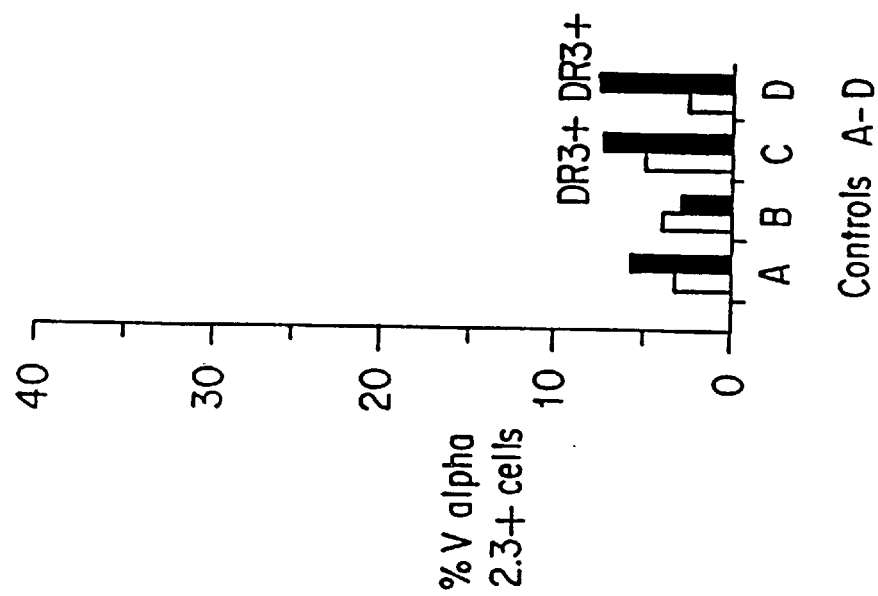

The present invention provides methods and compositions for diagnosis and therapy of sarcoidosis. The present inventors have discovered that sarcoidosis patients show selective compartmentalization to the lung of $V_\alpha 2.3^+CD^+$ T cells. As many as about one third of the accumulated $CD4^+$ T cells in bronchoalveolar lavage (BAL) of sarcoidosis patients specifically expressed $V_\alpha 2.3$ chains. This restricted V gene usage suggested the presence of an antigen which specifically stimulated pulmonary $V_\alpha 2.3^+CD4^+$ in sarcoidosis. In contrast, no significant compartmentalization of such T cells occurs in healthy subjects.

The present inventors further have discovered a striking correlation between the accumulation of $V_\alpha 2.3^+CD4^+$ T cells in the lung and the HLA-DR3(w17), DQw2 haplotype. Thus, the present inventors have discovered in a subgroup of sarcoidosis patients, two of the structures in the specific trimolecular complex comprising the TCR, the MHC molecule and the antigen. According to the present invention, the $V_\alpha 2.3^+CD4^+$ T cells which selectively accumulate in the lung of sarcoidosis patients are considered to play a pathophysiologic role in the disease process by directly or indirectly mediating the sarcoidosis disease.

Furthermore, a correlation between the localized $V_\alpha 2.3^+ CD4^+$ T cells and the time course of the disease discovered by the present inventors strengthens the association with the disease. Thus, enumeration of T cells expressing the TCR $V_\alpha 2.3$ in various cell populations is useful in diagnosing or predicting the course or response to therapy of sarcoidosis.

Thus, the present invention provides diagnostic and therapeutic approaches and agents for sarcoidosis based on the selective presence of a select T cell subpopulation bearing the $V_\alpha 2.3$ variant of the $TCR\alpha$ chain. These approaches and reagents are described more fully below.

5.1. Antibodies

Antibodies as well as fragments, derivatives, or analogues thereof, specific for an epitope of the $V_\alpha 2.3$ region of a human TCR α chain may be utilized in the diagnosis and therapy of sarcoidosis.

The term "antibody" is meant to include polyclonal antibodies, monoclonal antibodies (mAbs), and chimeric antibodies (see below). Preferred antibodies are mAbs, which may be of any immunoglobulin class including IgG, IgM, IgE, IgA, and any subclass or isotype thereof. Preferred antibodies for therapeutic use include antibodies of the IgG2a or IgG2b isotype (Rashid et al., 1992, *J. Immunol.* 148: 1382–1388).

The term "antibody" is also meant to include both intact molecules as well as fragments thereof which bind the antigen, such as, for example, $F(ab')_2$, Fab', Fab and Fv. These fragments lack the Fc fragment of an intact antibody molecule, clear more rapidly from the circulation, and may have less non-specific tissue binding than an intact antibody (Wahl et al., 1983, *J. Nucl. Med.* 24:316–325), properties which may be desirable for particular therapeutic or diagnostic utilities. It will be appreciated that these antigen-binding or epitope-binding fragments of the antibodies useful in the present invention may be used for the detection and quantitation of TCR proteins or peptides, or cells expressing the TCR proteins, as disclosed herein for intact antibody molecules. Such fragments are typically produced by proteolytic cleavage, using enzymes such as papain (to produce Fab fragments) or pepsin (to produce $F(ab')_2$ fragments) or by reducing the disulfide bridges.

The mAbs of the invention are reactive with a variable region of the $V_\alpha 2.3$ variant of the α a chain of the TCR. In a specific embodiment, mAb F1 as deposited with the ATCC and assigned accession number HB 11176 is used. The $V_\alpha 2.3$-specific mAbs of the present invention enables the analysis of the expression of the $V_\alpha 2.3$ gene in a biological sample.

Various chemical or biochemical derivatives of the antibodies or antibody fragments of the present invention can also be produced using known methods. One type of derivative which is diagnostically useful is an immunoconjugate comprising an antibody molecule, or an antigen-binding fragment thereof, to which is conjugated a detectable label such as a radioisotope, a fluorescent dye or another tracer molecule. A therapeutically useful immunoconjugate comprises an antibody molecule, or an antigen-binding fragment thereof, conjugated to a therapeutically useful molecule such as a cytotoxic drug or a toxic protein (see, for review: Dillman, R. O., Ann. Int. Med. 111:592–603 (1989)). Such antibody derivatives are discussed in more detail below.

The antibody, fragment or derivative useful in the present invention, may be prepared by using any of a number of techniques well-known in the art. For producing a mAb, any method which provides for the production of antibody molecules by continuous cell lines in culture may be used. These methods include, but are not limited to,the hybridoma technique originally described by Kohler and Milstein, (1975, *Nature* 256:495–497), and the more recent human B cell hybridoma technique (Kozbor et al., 1983, *Immunol. Today* 4:72), EBV-hybridoma technique (Cole et al., 1985, *Monoclonal Antibodies and Cancer Therapy*, Alan R. Liss, Inc., pp. 77–96), and trioma techniques. A hybridoma of rodent origin producing the mAbs of this invention may be cultivated in vitro or in vivo. For an overview of antibody production methods, see: Hartlow, E. et al., *Antibodies: A Laboratory Manual*, Cold Spring Harbor Laboratory Press, Cold Spring Harbor, N.Y., 1988.

In one embodiment, the antibody of the present invention is a human mAb. Human mabs may be made by any of a number of techniques known in the art (e.g., Teng et al., 1983, *Proc. Natl. Acad. Sci. U.S.A.* 80:7308–7312; Kozbor et al., supra; Olsson et al., 1982, *Meth. Enzymol.* 92:3–16).

In another embodiment, the antibody is a chimeric antibody, preferably a mouse-human chimeric antibody, wherein the heavy and light chain variable regions are derived from a murine mAb and the constant regions are of human origin. The chimeric antibodies of this invention have both the TCR-recognizing specificity of the mouse Mab and the biological properties of human antibodies, which include resistance to clearance in the human and lower immunogenicity for humans, allowing multiple treatments. Methods for producing chimeric antibody molecules are disclosed, for example, in Gorman et al., PCT Publication WO 92/06193 (Apr. 16, 1992); Cabilly et al., U.S. Pat. No. 4,816,567 (Mar. 28, 1989) and EPO Publication EP125023 (Nov. 14, 1984); Taniguchi et al., EPO Publication EP171496 (Feb. 19, 1986); Morrison et al., EPO Publication EP173494 (Mar. 5, 1986); Neuberger et al., PCT Publication WO 86/01533 (Mar. 13, 1986); Kudo et al., EPO Publication EP184187 (Jun. 11, 1986); Robinson et al., PCT Publication WO 87/02671 (May 7, 1987); Boulianne et al., *Nature* 312:643–646 (1984); Morrison, *Science* 229:1202–1207 (1985); Neuberger et al., *Nature* 314:268–270 (1985); Takeda et al., *Nature* 314:452–454 (1985); Oi et al., *BioTechniques* 4:214 (1986); and Liu et al., *Proc. Natl. Acad. Sci. USA* 84:3439–3443 (1987).

For human therapeutic purposes, mAbs or chimeric antibodies can be "humanized" by producing human constant region chimeras, where even parts of the variable regions, in particular the conserved or framework regions of the antigen-binding domain, are of human origin, and only the hypervariable regions are non-human. See for example, Winter, UK Patent Publication GB 2188638A (Oct. 7, 1987); Harris et al., PCT Publication WO 92/04381 (Mar. 19, 1992); Gorman et al., supra; Riechmann et al., 1988, *Nature* 332:323–327.

In yet another further embodiment, the antibody is a single chain antibody formed by linking the heavy and light chain fragment of the Fv region via an amino acid bridge, resulting in a single chain polypeptide (Bird, 1988, *Science* 242:423–426; Huston et: al., 1988, *Proc. Natl. Acad. Sci. USA* 85:5879–5883: and Ward et al., 1989, *Nature* 340:544–546).

Antibody molecules or fragments may be purified by known techniques, e.g., immunoabsorption or immunoaffinity chromatography, for example, using Staphylococcal protein A, or chromatographic methods such as HPLC (high performance liquid chromatography), or a combination thereof, etc. In a preferred method, the anti- $V_\alpha 2.3$ mAb, preferably F1 (produced by the hybridoma line deposited in the ATCC under accession number #HB 11176), is purified from culture supernatant or ascites fluid.

Once antibodies of the desired specificity are generated, they may be used to identify and select other antibodies having the same or cross-reactive epitope specificity. For example, a new antibody is tested by measuring its ability to inhibit the binding of an antibody of known specificity to its epitope. Various competitive binding assays known in the art can be used.

The isotype of the antibody can be selected during hybridoma production or by appropriate recombinant methods well-known in the art to achieve a desired effector function mediated by the Fc portion of the immunoglobulin heavy chain. For example, certain isotypes, such as IgG2a, have superior activity in antibody-dependent cellular cytotoxicity. Likewise, certain isotypes, such as IgG2a, are more readily eliminated from the circulation through Fc receptors on cells of the reticuloendothelial system and are therefore more efficient at removing an undesired antigen or target cell from sites of active disease (Rashid et al., supra). Accordingly, depending on the intended use, a particular antibody isotype may be preferable to others, as can be readily ascertained by one of ordinary skill in the art without undue experimentation.

As used herein, an antibody reactive with the "V region" of the TCR shall be construed to be an antibody reactive with an epitope of the V region, a combination epitope of the V region, or a combination epitope of the V-D or V-D-J regions. An antibody reactive with a V region of a TCR may recognize an idiotypic determinant, a clonotypic determinant, or, preferably, may recognize a minor framework region expressed by a discrete subset of T lymphocytes. An "anti-clonotypic" antibody reacts only with a determinant ("clonotypic determinant) of a particular clone of T cells, generally that clone against which it was raised (Acuto et al., *Cell* 34:717–726 (1988); Meuer et al. *Proc. Natl. Acad. Sci.* 81:1509–1513 (1984); Meuer et al., *Ann. Rev. Immunol.* 2:23–50 (1984)). Anti-clonotypic antibodies are also referred to as anti-idiotypic antibodies. "Minor framework region" refers to a region of the TCR which is not shared by all TCR molecules, but is also not unique to a particular T cell clone. Preferred anti-TCR a mAbs recognize members of the $V_\alpha 2$ family, most preferably, $V_\alpha 2.3$. Preferably, such an antibody is reactive with a unique epitope on a $V_\alpha 2.3$ variable region of the α chain of the TCR.

5.2. Diagnostic Use of Antibodies

The antibodies and fragments described herein are useful for diagnostic or research purposes in various immunoassays well-known in the art. The antibodies, or fragments of antibodies, useful according to the present invention may be used to quantitatively or qualitatively detect the presence of cells which express the TCR $V_\alpha 2.3$ gene, or to measure the levels of TCR $V_\alpha 2.3$ protein present in a sample. This can be accomplished by immunofluorescence techniques employing a fluorescently labeled antibody (see below) coupled with light microscopic, flow cytometric, or fluorimetric detection.

The antibodies (or fragments or derivatives thereof) useful in the present invention may be employed histologically, as in immunohistochemical staining, immunofluorescence or immunoelectron microscopy, for in situ detection of the TCR molecule.

One way of measuring the reactivity of a TCR epitope with a specific antibody of the present invention is by enzyme immunoassay (EIA) such as an enzyme-linked immunosorbent assay (ELISA) (Voller, A. et al., *J. Clin. Pathol.* 31:507–520 (1978); Butler, J. E., *Meth. Enzymol.* 73:482–523 (1981); Maggio, E. (ed.), *Enzyme Immunoassay*, CRC Press, Boca Raton, Fla., 1980). The enzyme, either conjugated to the antibody or to a binding partner for the antibody, when later exposed to an appropriate substrate, will react with the substrate in such a manner as to produce a chemical moiety which can be detected, for example, by spectrophotometric, fluorimetric or by visual means.

A preferred method of enumerating total TCR $V_\alpha 2.3$ chain is performed using detergent treated whole blood samples or isolated T cell or CD4$^+$ T cell populations. In particular $V_\alpha 2.3$-bearing subset may be detected from a sample by adding the cells (or whole blood) to wells of a 96 well microplate previously coated with 5 μg/ml of coating antibody. Coating antibody is either a negative control or an anti-major framework antibody to detect total a chain or a TCR V region specific mAb such F1 to detect a the $V_\alpha 2.3$ subset. An enzyme conjugated antibody, which recognizes a different epitope, for example, an epitope of the α or β a chain C region is used as a detection antibody. The assay format is described in Rittershaus C. W., PCT Publication WO 92/08981 (May 29, 1992).

Detection of the TCR $V_\alpha 2.3$ protein or cells expressing the protein may be accomplished using any of a variety of other immunoassays. For example it is possible to detect antibody binding to TCR V region through the use of a radioimmunoassay (RIA) (see, for example, Weintraub, B., Principles of Radioimmunoassays, Seventh Training Course on Radioligand Assay Techniques, The Endocrine Society, March, 1986, pp. 1–5, 46–49 and 68–78).

It is also possible to label the antibody in which binding is measured using radioactive, fluorescent, chemiluminescent or bioluminescent conjugated antibodies.

A variety of immunoassay formats is available, for either EIA or RIA systems. For example, assays may be competitive or non-competitive. Two site or sandwich assays may be used, either "forward", "simultaneous" or "reverse" assays, which are well-known in the art.

Additional types of immunoassays include precipitin reactions, gel diffusion precipitin reactions, immunodiffusion assays, agglutination assays, complement fixation assays, immunoradiometric assays, protein A immunoassays, and immunoelectrophoresis assays.

Binding of the antibody, or fragment or derivative thereof to the TCR epitope for which it is specific may be accomplished and/or detected in vitro or in vivo. In vitro binding, as described above, may be performed using histologic specimens, or fractions or extracts of tissue or fluid, including substantially purified T cells or selected subsets of T cells, preferably CD4$^+$ T cells. In vivo binding may be achieved by administering the antibody (or fragment or derivative) by any route or means known in the art, including but not limited to intravenous, intraperitoneal, intranasal, and intraarterial, such that specific binding may be detected. For detection of the TCR chain in cells in the lung, intrapulmonary administration, such as by inhalation of a spray or mist, may be used.

Imaging techniques can be used in vivo, wherein the antibody, derivative or fragment is bound to a detectable label capable of in vivo localization. Many different labels and methods of labeling are known in the art.

The present invention provides method for diagnosing sarcoidosis based on detecting the specific binding of a mAb, or a derivative or fragment thereof, to T cells expressing the TCR $V_\alpha 2.3$ chain in a biological sample from a subject suspected of having the disease. Biological samples which may be tested according to the present invention include any body fluid, such as peripheral blood, plasma, cerebrospinal fluid, lymph, peritoneal fluid, or pleural fluid, and the like, or any body tissue or extract thereof. Preferably samples for the diagnostic methods of the present invention include blood, bronchoalveolar lavage fluid, lymph, lymph node tissue and lung tissue.

According to the present invention, sarcoidosis may be diagnosed in a subject by detecting the increased presence of T cells expressing $V_\alpha 2.3$, in particular CD4$^+$ cells expressing $V_\alpha 2.3$, in a biological sample, such as bronchoalveolar lavage fluid, from the subject as compared to a "baseline sample." As used herein, the term "baseline sample" refers to a sample from a normal, healthy individual who does not have sarcoidosis (or who has a disease unrelated to sarcoidosis not known to involve any changes in the distribution of presence of $V_\alpha 2.3^+$ cells) or a sample from the subject prior to onset of the disease or at a time of remission of the disease. A baseline sample may also be a mixture or average of samples from a general population. In one embodiment, the biological sample being tested is from the site of disease, generally lung tissue or bronchoalveolar lavage fluid, and the baseline sample is the peripheral blood.

Alternatively, such diagnosis may be achieved by detection of the presence of nucleic acid sequences characteristic of the TCR $V_\alpha 2.3$ regions using molecular techniques. Preferably, such molecular diagnosis is achieved by detecting the presence of nucleic acid sequences homologous to a gene encoding a part of the variable region of TCR $V_\alpha 2.3$ in mRNA in a patient sample. The nucleic acid sequence (SEQ ID NO:1) of TCR $V_\alpha 2.3$ DNA is shown in FIG. 4, and the amino acid sequence (SEQ ID NO:2) is shown in FIG. 5. One skilled in the art could readily design diagnostic tests to detect the presence of increased T cells expressing $V_\alpha 2.3$ as described here. In one embodiment, mRNA encoding $V_\alpha 2.3$ in a sample is detected by Northern analysis, by contacting an RNA-containing preparation with a nucleic acid probe specific for TCR $V_\alpha 2.3$ and detecting the hybridization therebetween. In another embodiment, DNA encoding $V_\alpha 2.3$ in a sample is detected by Southern analysis, by contacting a DNA-containing sample with a nucleic acid probe specific for TCR $V_\alpha 2.3$ and detecting the hybridization therebetween. Molecular approaches used to correlate TCR gene expression with disease include:

(1) producing and analyzing cDNA libraries obtained from the disease-related T cells obtained from one or more subjects having the disease, to determine the presence of frequently used or "dominant" TCR genes;
(2) Southern analysis of disease samples to determine whether specific genetic polymorphisms (e.g., RFLPs) or oligoclonal TCR rearrangements exist;
(3) analysis of disease samples by cDNA synthesis, PCR amplification, and slot blot hybridization procedures;
(4) in situ nucleic acid hybridization of TCR probes to T cells without prior culture of these cells.

It should be understood that the diagnostic methods of the present invention are best used in conjunction with other known diagnostic methods to obtain a comprehensive patient diagnosis. Although the precise pathogenesis of sarcoidosis is not known, clinical evidence suggests that the lung is the first site of involvement. The process extends through the lymphatics to the hilar and mediastinal lymph nodes. Radiographically apparent mediastinal and hilar lymph node involvement occurs in about 90% of sarcoidosis patients. Thus, a diagnosis of sarcoidosis; may be made based on the methods of the present invention together with conventional diagnostic recognition of the clinical features of sarcoidosis, such as those described above. For a more complete description of clinical aspects of sarcoidosis, see, for example, Neville, E. et al., *Quart. J. Med.* 208:525 (1983); Fanburg, B. L., In: *Lung Biology in Health and Disease*, C. Lefant, ed., M. Dekker Inc., vol. 20 (1983); and Brostoff, J. et al., *Clinical Immunology*, Gower Medical Publishing (1991), which references are herein incorporated by reference. As with any diagnostic criteria, the parameters disclosed in the present invention may not be sole determinants, or pathognomonic, of sarcoidosis.

5.3. Therapeutic Use Antibodies of the Invention

As mentioned above, the present invention is also useful in the therapy of sarcoidosis. The therapeutic embodiments of the present invention based on the correlation between the disease and preferential use of the $V_\alpha 2.3$ gene in T cells associated with the disease or preferential proliferation and/or accumulation of CD4$^+$V$_\alpha$2.3$^+$ T cells in the lungs of patients with sarcoidosis. The antibodies, fragments or derivatives of the present invention are therapeutically useful in part because they may interfere with the binding of the T cell, via its TCR, to the MHC/antigen complex needed for initiation or propagation of the inflammatory process underlying sarcoidosis.

T cells of the subset associated with sarcoidosis may recognize a true "sarcoidosis antigen" or an disease-associated antigen (such as certain viral or bacterial antigens). Such cells may be cloned and expanded or immortalized in culture by methods well-known in the art. The cultured cells serve as the source of cell-surface TCR chains for making yet additional antibodies or as the source of cDNA encoding the appropriate TCR for molecular identification of TCR usage. Such cDNA is cloned and expressed by methods well known in the art. (See, for example, Sambrook, J. et al., (*Molecular Cloning: A Laboratory Manual,* 2nd Edition, Cold Spring Harbor Press, Cold Spring Harbor, N.Y. (1989)).

Treatment of an individual according to this invention with antibodies, fragments or derivatives comprises parenterally administering a single dose or multiple doses of the antibody, fragment or derivative. The effective dose is a function of the individual antibody (or fragment or derivative), the presence and nature of a conjugated therapeutic agent, the subject and his clinical status. Effective doses of the antibodies, fragments or derivatives of this invention for use in preventing, suppressing, or treating an immune-related disease are in the range of about 1 ng to 100 mg/kg body weight. A preferred dose range is between about 10 ng and 10 mg/kg. A more preferred dose range is between about 100 ng and 1 mg/kg.

The route of administration may include intravenous (IV), subcutaneous (SC), intramuscular, intrapulmonary, intraperitoneal (IP), intranasal, intracerebroventricular, intrathecal, intradermal, or other known routes.

As mentioned above, the antibody or antigen-binding fragment thereof can be coupled to cytotoxic proteins, including ribosomal inhibitory proteins such as Ricin-A, Pseudomonas toxin, and Diphtheria toxin, as well as other proteins such as tumor necrosis factor. Toxins conjugated to antibodies or other ligands, are known in the art (see, for example, Olsnes, S. et al., *Immunol. Today* 10:291–295 (1989)). Since antibody to a particular TCR epitope will react with a much smaller proportion of total lymphocytes than the more broadly-reactive immunotoxins used to date, higher doses of a toxin-conjugated anti-TCR antibody will be tolerated by patients, or conversely, lower doses will be effective.

In a preferred embodiment, ricin A chain is conjugated to a anti-$V_\alpha 2.3$ antibody resulting in an immunoconjugate capable of binding to the TCR of lymphocytes which are a causative agent or pathophysiologically significant agent of sarcoidosis and destroying the cells, thereby treating the disease. Effective doses of a ricin A conjugated monoclonal anti-TCR antibody are in the range of about 0.005 to 0.5 mg/kg/day, with the preferred dose in the range of about 0.05 to 0.2 mg/kg/day.

The anti-TCR antibody, fragment or derivative can be conjugated to additional types of therapeutic moieties including, but not limited to, radionuclides and cytotoxic drugs. Non-limiting examples of radionuclides which can be coupled to antibodies and delivered in vivo to sites of antigen include $^{212}$Bi, $^{131}$I, $^{186}$Re, and $^{90}$Y. Such radionuclides exert their cytotoxic effect by locally irradiating the cells, leading to various intracellular lesions, as is well-known in the art of radiotherapy.

Cytotoxic drugs which can be conjugated to antibodies and subsequently used for in vivo therapy include, but are not limited to, daunorubicn, doxorubicin, methotrexate, and mitomycin C. For a fuller exposition of these classes of drugs which are known in the art, and their mechanisms of action, see Goodman, A. G., et al., *Goodman and Gilman's The Pharmacological Basis of Therapeutics,* 7th Ed., Macmillan Publishing Co., (1985).

The therapeutic approaches disclosed herein are based on any of a number of possible mechanisms by which the antibodies, fragments or derivatives of the present invention may act to achieve the therapeutic benefits. The present inventors do not intend to be bound by any particular theory as to mechanism of action. For example, in one embodiment, an antibody directed against TCR $V_\alpha$2.3 can be used, alone or conjugated to a toxic agent, to remove the undesired T cells. In another embodiment, the antibody is administered therapeutically to block the interaction of effector T cells with the antigen for which they are specific, thereby modulating a deleterious immune response.

An administered antibody, fragment or derivative of the present invention may act by binding a $V_\alpha$2.3 molecule in vivo and marking the T cell bearing that TCR chain for elimination by the one or another host defense system such as the reticuloendothelial system, or through antibody-dependent cellular cytotoxicity.

For the antibody, fragment or derivative of the present invention to be useful in therapy, it must have the ability to recognize and either modulate or lead to the destruction of the disease-related T cell subset.

First generation treatments based on anti-TCR V region antibody therapeutics may be developed using knowledge of the correlation between sarcoidosis and the expression of a the TCR $V_\alpha$2.3 gene subfamily in subjects having the disease. Such therapeutics offer an improvement over current procedures. Prior to the present invention, therapeutic options for sarcoidosis included: (a) no therapy with possible spontaneous resolution; (b) treatment with corticosteroids; (c) alternative forms of anti-inflammatory or immunosuppressive therapy, including nonsteroidal anti-inflammatory drugs, cyclosporin A, azathioprine, cyclophosphamide, chlorambucil, chloroquine, methotrexate, and calcium chelating agents. However, none of these drugs listed in (c) have clearly improved efficacy over corticosteroids. The therapeutic methods of the present invention have the distinct advantage over the prior art methods of treating sarcoidosis in that the methods of the present invention target only the particular T cell subset expressing a particular TCR Vα subfamily. These methods of the present invention more closely approach the goal of modulating only the disease-related T cells, while sparing or not affecting other T cells in the subject, to achieve a greater specificity of therapy.

For measuring preventative, suppressive, or therapeutic benefit of the antibody (or TCR peptide; see below) compositions of this invention in humans, certain clinical outcome measures are used. In sarcoidosis, clinical and laboratory parameters include: (a) clinical disability; (b) pulmonary function, (c) pulmonary radiography, e.g., presence of peripheral and/or parenchymal lung lesions; (d) lymph node radiography, e.g., unilateral or bilateral enlargement; and (e) cytological examination of bronchoalveolar lavage fluid, e.g., presence and number of lymphocytes or T cell subsets.

5.4. T Cell Receptor-Based Peptides and Their Therapeutic Application

The present invention is also directed to treating sarcoidosis using a peptide corresponding to a portion of the TCR expressed on lymphocytes associated with the disease, preferably the $V_\alpha$2.3 chain. The present inventors do not intend to be bound by the mechanism(s) by which the TCR protein or peptide acts on the immune system. According to one embodiment, these TCR "mimic" peptides are able to interfere with the binding of the MHC/antigen complex (or the antigen alone) needed for initiation or propagation of the immunological stages of the inflammatory process of sarcoidosis. Alternatively or additionally, the TCR peptides stimulate the immune system to respond to the TCR on the disease-mediating T cells, resulting in a therapeutic benefit associated with such "counter-autoimmunity."

In general, the TCR peptide sequence represents a portion of the TCR itself and preferably corresponds to a portion of the TCR which is extracellular, exposed to antibody or other T cells, and is of biological importance in the activity of the T cell bearing the TCR. For the purposes of this invention, the peptide is preferably immunogenic, that is, capable of inducing an immune response when injected into a subject. It is understood that the protein or peptide comprising the TCR peptide according to this invention can be used alone or bound to, or contained within the sequence of, a longer peptide. The longer peptide may carry additional sequence derived from the $V_\alpha 2.3$ chain or may include sequences of an unrelated peptide, such as a carrier protein used to enhance the immunogenicity of the TCR oligopeptide. Such carriers are well known in the art and include heterologous proteins such as, for example, keyhole limpet hemocyanin (KLH), bovine serum albumin, tetanus toxoid and the like. Also included within the scope of this invention are methods and compositions which utilize the TCR peptide conjugated to an antibody or the peptide conjugated to a toxin. Toxins useful for such compositions and methods include the ribosomal inhibitory proteins, such as, for example, the ricin A chain, Pseudomonas toxin, Diphtheria toxin, as well as other proteins such as tumor necrosis factor. Toxins conjugated to antibodies or other ligands, are known in the art (see, for example, Olsnes, S. et al., supra).

One peptide according to the present invention has 135 amino acids and includes the leader sequence, and the V and J regions of $V_\alpha 2.3$. The amino acid sequence (in single letter code) of this peptide is:

MMISLRVLLVIL-
    WLQLSWVWSQRKEVEQDPGPFNVPE-
    GATVAFPNCTYSNS ASQSFFWYRQDCRKEP-
    KLLMSVYSSGNEDGRFTAQLNRASQYISLLIRDS
    KLSDSATYLCVVNIRPGNTPLVFGKGTRLSVIPNI
    (SEQ ID NO:2, see FIG. 5).

A preferred peptide corresponds to the VJ region of SEQ ID NO:2, beginning at residue 24, and has the amino acid sequence:

KEVEQDPGPFNVPEGATVAFNCTYSN-
    SASQSFFWYRQDCRKEPKLLMSVY SSGNEDGR-
    FTAQLNRASQYISLLIRDSKLSDSATYL-
    CVVNIRPGNTPLVF GKGTRLSVIPNI (SEQ ID NO:3)

Alternatively, the peptide can correspond to the V region of SEQ ID NO:2, having the amino acid sequence:

KEVEQDPGPFNVPEGATVAFNCTYSN-
    SASQSFFWYRQDCRKEPKLLMSVY SSGNEDGR-
    FTAQLNRASQYISLLIRDSKLSDSATYLCVVN (SEQ ID NO:4.)

In another embodiment, the peptide corresponds to the J region of SEQ ID NO:2, having the amino acid sequence:
IRPGNTPLVFGKGTRLSVIPNI (SEQ ID NO:5)

In a preferred embodiment, the peptide corresponds to at least part of one of the three complementarity determining regions (CDRs) of the TCR α chain. The CDRs of the TCR are defined by analogy to the structure of the immunoglobulin molecule wherein CDRs comprise the amino acid sequences of the heavy or light chain V regions which contact the antigen and constitute crucial portions of the antigen-binding site. All three TCR CDRs are believed to participate in binding to antigen and MHC (Davis, M. M., et al.; Claverie, J. M., et al., *Immunol. Today* 10:10–14 (1989)).

Thus, a peptide corresponding to CDR1 of the TCR $V_\alpha 2.3$ region is a 34-mer with the sequence from residues 24–57 of SEQ ID NO:2:

KEVEQDPGPFNVPEGATVAFNCTYSNSASQSFFW (SEQ ID NO:6)

A peptide corresponding to CDR2 of the TCR $V_\alpha 2.3$ region is a 47-mer with the sequence from residues 58–104 of SEQ ID NO:2:

YRQDCRKEPKLLMSVYSSGNEDGR-
    FTAQLNRASQYISLLIRDSKLSD (SEQ ID NO:7)

A peptide corresponding to CDR3 of the TCR $V_\alpha 2.3$ region is a 31-mer with the sequence from residues 105–135, including both the V and J region, of SEQ ID NO:2: SATYLCVVNIRPGNTPLVFGKGTRLSVIPNI (SEQ ID NO:8).

By directing the immune response of the subject to generate either protective antibodies or regulatory T cells which are specific to one of the CDRs of the TCR $V_\alpha 2.3$ region, the likelihood of disrupting necessary binding or recognition events between the sarcoidosis-associated T cell and the yet unknown autoantigen and/or the MHC is increased.

In a preferred aspect, the size of the peptide selected for use in this invention is sufficient for conferring antigenicity or immunogenicity, while maintaining the minimal epitope structure such that a T cell or antibody specific for the TCR peptide will recognize and react with the TCR $V_\alpha 2.3$ chain on an intact T cell. For example, peptides of this invention, in order to be sufficiently immunogenic and to have a high probability of including the relevant epitope of the TCR which can lead to modulation of T cell activity, are of the range of at least about 6 amino acids, more preferably at least about 15–30 amino acids, although peptides of differing length are also contemplated. For example, a 21 amino acid TCR peptide present on the TCR β chain associated with experimental allergic encephalomyelitis (EAE) has been used to treat EAE successfully (Vandenbark, A. A., et al., *Nature* 341:541–544 (1989); Vandenbark, A., PCT Publication WO 91/01133 (Feb. 7, 1991); see, also Janeway, C. A., *Nature* 341:482–483 (1989)). Others have reported that even shorter peptides of 8 or 11 amino acids, corresponding to the β chain VDJ region or the Jα region proved effective as "vaccines" for either preventing or reducing the severity of EAE in a rat model (Howell, M. D. et al., *Science* 246:668–671 (1989); Howell, M. D. et al., PCT Publication WO 92/12996 (Aug. 6, 1992)).

By examining a variability plot of TCR α chains, such as that disclosed by Kabat, E. et al., *SEQUENCES OF PROTEINS OF IMMUNOLOGICAL INTEREST*, 5th Edition, 1991, NIH, U.S. Dept. of Health and Human Services Publication #913242), one of ordinary skill in the art will discern the regions which possess the greatest variability, and from this information, can determine the peptides which comprise 3 CDRs of the TCR α chain. Thus, preferred peptides for therapeutic uses in accordance with the present invention include the following five peptides (designated P1–P5) corresponding to fragments of the TCR VJ α2.3 region from SEQ ID NO:2:

```
Residues
P1: 24-44    KEVEQDPGPFNVPEGATVAFN              (SEQ ID NO:9)

P2: 45-61    CTYSNSASQSFFWYRQD                  (SEQ ID NO:10)

P3: 62-77    CRKEPKLLMSVYSSGN                   (SEQ ID NO:11)

P4: 78-109   EDGRFTAQLNRASQYISLLIRDSKLSDSATYL   (SEQ ID NO:12)

P5: 110-135  CVVNIRPGNTPLVFGKGTRLSVIPNI         (SEQ ID NO:13)
```

In light of the observations described above in the treatment of other immunological diseases associated with a particular TCR, therapeutic peptides as short as about 15 amino acids from the α chain V or J region may be used to prevent the progression of sarcoidosis. It may also be possible to prevent the onset of sarcoidosis by such treatment if appropriately susceptible individuals, for example those expressing HLA-DR3(w17), can be identified. Identification of those individuals having a particular HLA type can be performed using routine methods well-known in the art. For detailed methods of serological and biochemical analysis of HLA, see *American Society for Histocompatibility and Immunogenetics Laboratory Manual*, 2nd Edition, Zachary, A. A. et al., eds., 1990 (herein incorporated by reference). For methods of DNA and molecular analysis of HLA, see, for example, Carlsson, B. et al., *Hum. Immunol.* 20:95 (1987); Bidwell, J. L. et al., *Baillieres Clin. Haematol.* 3:355–384 (1990); Tiercy, J. M. et al., *Blood Rev.* 4:9–15 (1990); Wordsworth, P., *Immunol. Lett.* 29:37–39 (1991); Shaffer, A. L. et al., *Tiss. Antigens* 39:84–90 (1992) (which references are herein incorporated by reference).

Also intended within the scope of this invention is a "functional derivative" of the TCR α chain peptide, including a "fragment," "variant," "analogue," or "chemical derivative" of the peptide, which terms are defined below.

A "fragment" refers to any subset of the molecule, that is, a shorter peptide. A "variant" of the peptide refers to a molecule substantially similar to either the entire peptide or a fragment thereof. Variant peptides may be conveniently prepared by direct chemical synthesis of the variant peptide, using methods well-known in the art. Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see EPO Publication EP75444). At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

Another group of variants are those in which at least one amino acid residue in the protein molecule, and preferably, only one, has been removed and a different residue inserted in its place. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. The types of substitutions which may be made in the TCR $V_\alpha 2.3$ a chain protein or peptide molecule may be based on analysis of the frequencies of amino acid changes between a homologous protein of different species, such as those presented in Table 1–2 of Schulz et al. (supra) and FIG. 3–9 of Creighton (supra). Based on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positvely charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Glycine is the only residue lacking any side chain and thus imparts flexibility to the chain. Proline, because of its unusual geometry, tightly constrains the chain. Cysteine can participate in disulfide bond formation which is important in protein folding. Tyrosine, because of its hydrogen bonding potential, has some kinship with serine and threonine.

Substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of glycine and/or proline by another amino acid or deletion or insertion of glycine or proline; (b) substitution of a hydrophilic residue, e.g., serine or threoine, for (or by) a hydrophobic residue, e.g., leucine, isoleucine, phenylalanine, valine or alanine; (c) substitution of a cysteine residue for (or by) any other residue; (d) substitution of a residue having an electropositive side chain, e.g., lysine, arginine or histidine, for (or by) a residue having an electronegative charge, e.g., glutamic acid or aspartic acid; or (e) substitution of a residue having a bulky side chain, e.g., phenylalanine, for (or by) a residue not having such a side chain, e.g., glycine.

The activity of a TCR protein or peptide variant is then screened in a suitable screening assay for the desired characteristic. For example, a change in the immunological character of the peptide molecule, such as binding to a given anti-TCR mAb, is measured by a competitive type immunoassay. Changes in T cell recognition of the variant peptide is measured by a delayed hypersensitivity assay in vivo or a T cell proliferation assay in vitro, which are well-known in the art. Modifications of such peptide properties as redox or thermal stability, hydrophobicity, susceptibility to proteolytic degradation or the tendency to aggregate with carriers or into multimers are assayed by methods well known to the ordinarily skilled artisan.

An "analog" of a peptide refers to a non-natural molecule substantially similar to either the entire molecule or a fragment thereof.

A "chemical derivative" of a peptide of this invention contains additional chemical moieties not normally a part of the peptide. Covalent modifications of the peptides are included within the scope of this invention. Such modifications may be introduced into the molecule by reacting targeted amino acid residues of the peptide with an organic derivatizing agent that is capable of reacting with selected side chains or terminal residues. Such derivatized moieties may improve the peptide's solubility, absorption, biological half life, and the like. The moieties may alternatively eliminate or attenuate any undesirable side effect of the peptide and the like. Moieties capable of mediating such effects are disclosed, for example, in Remington's Pharmaceutical Sciences, 16th ed., Mack Publishing Co., Easton,

5.5. Antisense Oligonucleotides as Inhibitors of T Cells Expressing $V_\alpha 2.3$ By the term "antisense" is intended an RNA sequence, as well as a DNA sequence coding therefor, which is sufficiently complementary to a particular MRNA molecule ("sense" RNA) for which the antisense RNA is specific to cause molecular hybridization between the antisense RNA and the mRNA. The action of the antisense RNA results in specific inhibition of gene expression in the cell (see: Albers, B. et al., Molecular Biology of the Cell, 2nd Ed., Garland Publishing, Inc., New York, N.Y. (1989), in particular, pages 195–196, which reference is herein incorporated by reference).

An antisense nucleic acid of the present invention is preferably an oligonucleotide having at least about six nucleotides which can be double-stranded or single-stranded, RNA or DNA, or a modification of a derivative thereof, such as a nucleic acid containing nucleotide base analogues.

An oligonucleotide, between about 6 and about 100 bases in length, preferably at least about 15 nucleotides, and more preferably at least about 18 or about 25 nucleotides, and complementary to the target subsequence of the TCR $V_\alpha 2.3$ gene region (SEQ ID NO:1) may be synthesized by methods known in the art. For example, the antisense oligonucleotide may be synthesized from natural mononucleosides or, alternatively, from mononucleosides having substitutions at the non-bridging phosphorous bound oxygens (see below). In a pharmaceutical composition useful for treating sarcoidosis, the oligonucleotide of the present invention is combined with a pharmaceutically acceptable carrier.

Basic procedures for constructing recombinant DNA and RNA molecules in accordance with the present invention are disclosed by Sambrook, J. et al., supra).

Oligonucleotide molecules having a strand which encodes antisense RNA complementary to the a TCR $V_\alpha 2.3$ sequence can be prepared using procedures which are well known to those of ordinary skill in the art (Belagaje, R., et al., J. Biol. Chem. 254:5765–5780 (1979); Maniatis, T., et al., In: Molecular Mechanisms in the Control of Gene Expression, Nierlich, D. P., et al., Eds., Acad. Press, NY (1976); Wu, R., et al., Prog. Nucl. Acid Res. Molec. Biol. 21:101–141 (1978); Khorana, H. G., Science 203:614–625 (1979)). Additionally, DNA synthesis may be achieved through the use of automated synthesizers. Techniques of nucleic acid hybridization are disclosed by Sambrook et al. (supra), and by Haymes, B. D., et al., In: Nucleic Acid Hybridization, A Practical Approach, IRL Press, Washington, D.C. (1985)), which references are herein incorporated by reference.

An "expression vector" is a vector which (due to the presence of appropriate transcriptional and/or translational control sequences) is capable of expressing a DNA (or cDNA) molecule which has been cloned into the vector and of thereby producing an RNA or protein product. Expression of the cloned sequences occurs when the expression vector is introduced into an appropriate host cell. For expression of an antisense DNA in a human T cell, a eukaryotic expression vector is employed. Preferred promoters and additional regulatory elements, such as polyadenylation signals, are those which should yield maximum expression in T lymphocytes. To efficiently express an antisense RNA complementary to a TCR $V_\alpha 2.3$ sequence, a transcriptional control unit (promoter and polyadenylation signal) are selected which provide efficient expression in lymphoid cells or tissues, in particular in human T lymphocytes. Examples of useful viral and eukaryotic promoters include the promoter of the mouse metallothionein I gene (Hamer, D., et al., J. Mol. Appl. Gen. 1:273–288 (1982)); the TK promoter of Herpes virus (McKnight, S., Cell 31:355–365 (1982)); the SV40 early promoter (Benoist, C. et al., Nature 290:304–310 (1981), all of which references are incorporated by reference herein). The most preferred promoters for expression of antisense in T lymphocytes are the cytomegalovirus immediate early promoter, optionally used in conjunction with the bovine growth hormone polyadenylation signals, and the promoter of the Moloney-MuLV LTR, for use with a lympholtropic retrovirus. The metallothionein promoter has the advantage of inducibility.

A DNA sequence encoding the antisense RNA of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

According to the present invention, successful transfection of cells with DNA antisense to the TCR $V_\alpha 2.3$ gene may inhibit the development of, or activity of, T cell bearing this TCR. Thus, growth, differentiation, activation or lung localization of $V_\alpha 2.3$-bearing T cells may be prevented or inhibited. This antisense DNA must have sufficient complementarity to the $V_\alpha 2.3$ gene so that the antisense RNA can hybridize to the $V_\alpha 2.3$ DNA or mRNA and inhibit the gene's expression, regardless of whether the action is at the level of splicing, transcription or translation. Preferably, the oligonucleotide comprises between about 15 and about 100 nucleotides complementary to a part of SEQ ID NO:1and is preferably at least 18 or at least 25 nucleotides.

The antisense RNA of the present invention may be hybridizable to any of several portions of the target $V_\alpha 2.3$ DNA, including the coding sequence, 3' or 5' untranslated regions, or other intronic sequences, or to $V_\alpha 2.3$ mRNA. As is readily discernible by one of ordinary skill in the art, the minimal amount of homology required by the present invention is that sufficient to result in hybridization to the $V_\alpha 2.3$ DNA or mRNA and inhibition of transcription of the DNA or translation or function of the mRNA, while substantially not affecting the function of other essential mRNA molecules and the expression of other essential genes in the cells.

The antisense oligonucleotide of the present invention may include other appending groups such as peptides, or agents facilitating transport across cell membranes (Letsinger et al., *Proc. Natl. Acad. Sci. USA* 86:6553–6556; Lemaitre et al., *Proc. Natl. Acad. Sci. USA* 84:648–652 (1987); PCT Publication WO 88/09810 (Dec. 15, 1988)), hybridization cleavage agents (Krol et al., *BIoTechniques* 6:958–976 (1988)) or intercalating agents (Zon et al., *Pharm Res.* 5:539–549 (1988)).

In one embodiment, antisense RNA is delivered to a cell by transformation or transfection with a vector into which has been placed DNA encoding the antisense RNA with the appropriate regulatory sequences, including a promoter, which results in expression of the antisense RNA in a host cell. Means of delivery of such antisense RNA or antisense DNA are known (EPO Publication 248,531; PCT Publication WO 89/2110; Lemaitre et al., *Proc. Natl. Acad. Sci. U.S.A.*, 84:648–652 (1987); (Toulme et al., *Gene* 72:51–58 (1988).

In another embodiment, the antisense oligonucleotide is directly delivered to the cells, e.g., via receptor-mediated endocytosis, by formulation into a liposome which is taken up by cells, by direct injection into a cell, etc.

In addition to antisense oligonucleotides containing native nucleotides, the oligonucleotide of the present invention may include nucleoside or nucleotide analogues, having a modified sugar or modified phosphate backbone. Such analogues have the advantageous properties of resistance to nuclease hydrolysis and improved penetration into mammalian cells (Miller, P. S. et al., *Biochemistry* 20:1874–1880 (1981)). For example, an oligo(deoxyribonucleoside phosphonate) complementary to sequences of viral, bacterial or eukaryotic DNA blocks gene expression (Jayaraman, K. et al., *Proc. Natl. Acad. Sci. USA* 78:1537–1541 (1983); Blake, K. R. et al., *Biochemistry* 24:6139–6145 (1985); Miller, P. et al., *Feder. Proc.* 43:abstr. 1811 (1984); Smith, C. C. et al., *Proc. Natl. Acad. Sci. USA* 83:2787–2791 (1986)). Preferred analogues which make an oligonucleotide resistant to in vivo degradation nucleases have modified internucleoside linkages, for example, methylphosphonates, phosphorothioates, or 2'-O-methylribose or 1'-alpha- anomers. More generally, preferred analogues are mononucleoside analogues which result in an oligonucleotide which has improved diffusion through cell membranes or increased resistance to nuclease digestion within the body of a subject. Such nucleoside analogues are well-known in the art, and their use in the inhibition of gene expression are detailed in a number of references (Miller, P. S. et al., supra; Jayaraman, K. et al., supra; Blake, K. R. et al., supra; Smith, C. C. et al., supra). The entire antisense oligonucleotide molecule may be formed of such modified linkages, or only certain portions, such as the 5' and 3' ends, may be so affected, thereby providing resistance to exonucleases. Antisense molecules suitable for use in the present invention include but are not limited to dideoxyribonucleoside methylphosphonates (Mill, et al., *Biochemistry* 18:5134–5143 (1979)), oligodeoxynucleotide phosphorothioates (Matsukura et al., *Proc. Nat. Acad. Sci.*, 84:7706–10 (1987)), oligodeoxynucleotides covalently linked to an intercalating agent (Zerial et al., *Nuc. Acids Res.* 15:9909–9919 (1987)), oligodeoxynucleotide conjugated with poly-L-lysine (Leonetti et al., *Gene* 72:32–33 (1988), and carbamate-linked oligomers assembled from ribose-derived subunits (Summerton, J., *Antisense Nucleic Acids Conference* 37:44 (1989)).

5.6. Pharmaceutical Compositions and Their Administration

The preclinical and clinical therapeutic use of the present invention in the treatment of sarcoidosis will be best accomplished by those of skill, employing accepted principles of diagnosis and treatment. Such principles are known in the art, and are set forth, for example, in Braunwald, E. et al., eds., *Harrison's Principles of Internal Medicine*, 11th Ed., McGraw- Hill, publisher, New York, N.Y. (1987).

The antibodies, fragments and derivatives of the present invention, and the TCR V region peptides are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intrapulmonary, intranasal, intradermal, intramuscular, intraperitoneal, transdermal, or buccal routes. Alternatively, or concurrently, administration may be by the oral route. The pharmaceutical compositions can be administered parenterally by bolus injection or by gradual perfusion over time.

The dosage administered will be dependent upon the age, sex, health, and weight of the recipient, kind of concurrent treatment, if any, frequency of treatment, and the nature of the effect desired. The dose ranges for the administration of the compositions of the present invention are those large enough to produce the desired effect. The doses should not be so large as to cause adverse side effects, such as unwanted cross reactions, generalized immunosuppression, anaphylactic reactions and the like.

Preferred doses for humans range between about 0.0001–25 mg of antibody, fragment or derivative per kg body weight. Preferred doses of the TCR peptide for humans range between about 1–1000 mg per kg body weight.

In addition to the pharmacologically active components (i.e., antibody, fragment, or derivative, or TCR peptide), pharmaceutical compositions preferably contain suitable pharmaceutically acceptable carriers comprising excipients and auxiliaries which facilitate processing of the active compounds into preparations which can be used pharmaceutically. Such pharmaceutically acceptable carrier are sterile. Moreover, as used herein, the term pharmaceutically acceptable carriers does not include cell culture media, or any components not approved for use in humans.

Suitable formulations for parenteral administration include aqueous solutions of the antibody in water-soluble form, for example, water-soluble salts. In addition, suspensions of the antibody as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. The antibodies, fragments or derivatives of the invention are preferably formulated in purified form substantially free of aggregates and other protein materials, preferably at concentrations of about 1.0 ng/ml to 100 mg/ml.

The compositions are formulated using conventional pharmaceutically acceptable parenteral vehicles for administration by injection. These vehicles are nontoxic and therapeutic, and a number of formulations are set forth in Remington's Pharmaceutical Sciences, 16th ed., Mack Publishing Co., Easton, Pa. (1980). Non-limiting examples of excipients are water, saline, Ringer's solution, dextrose solution and Hank's balanced salt solution. Formulations according to the invention may also contain minor amounts of additives such as substances that maintain isotonicity, physiological pH, and stability.

To enhance delivery or bioactivity, the antibodies, fragment or derivative thereof, can be incorporated into liposomes using methods and compounds known in the art.

Having now generally described the invention, the same will be more readily understood through reference to the following examples which are provided by way of illustration, and are not intended to be limiting of the present invention, unless specified.

6. Example: Restricted $V_\alpha 2.3$ Gene Usage By CD4$^+$ T Lymphocytes In Bronchoalvelar Lavage Fluid From Sardoidosis Patients And Correlation With HLA-DR3

6.1. Materials and Methods

6.1.1. Subjects

The sarcoidosis population studied consisted of 11 patients with untreated sarcoidosis (median age: 29–46); 2 women). one was a smoker (no. 9); eight were non-smokers and two ex-smokers (>5 years). Six patients had clinically active sarcoidosis (nos. 1, 2, 4, 5, 10 and 11). Patients nos. 5, 6, 7 and 10 were reanalyzed six months after the initial investigation. During this period, patients nos. 6, 7 and 10 were all untreated. When reanalyzing these patients, nos. 1, 7 and 10 were clinically healthy. Patient no. 6 presented symptoms of coughing, low-grade fever and enlarged cervical lymph nodes (LN), one of which was extirpated. Four healthy volunteers (median age 36 (20–59); 3 women), all non-smokers were included as controls.

6.1.2. Bronchoalveolar Lavage

Sterile saline, 250 ml at 37° C., was instilled in five aliquots of 50 ml. The fluid was gently aspirated after each instillation and collected in a siliconized bottle kept on ice. The mean recovery of the instilled fluid was 73±5% in the sarcoidosis patients and 75±5% in the controls.

6.1.3. Cells

The BAL fluid was strained through a double layer of Dacron nets. Cells were pelleted by centrifugation at 400×g for 5 min at 4° C. and resuspended in Hanks balanced salt solution (HBSS). The median total cell concentrations were 125±10$^6$(interquartile ranges (i.q.r.) 78–218) cells/l in samples from the investigated sarcoidosis patients, and 68×10$^6$(45–93) cells/l from the controls. The median proportions of macrophages/monocytes, lymphocytes and neutrophils were 77% (64–87), 22% (12–34) and 0.8% (0.3–1.4) in the sarcoidosis patients and 91% (87–93) 8% (6–10) and 1.0% (0.7–1.3) in the controls, respectively. Peripheral blood mononuclear cells (PBMC), separated from heparinized peripheral blood by Ficoll-Hypaque (Pharmacia, Uppsala, Sweden) gradient centrifugation, were washed twice in RPMI-1640 medium (Gibco, Paisley, Scotland) and diluted in PBS.

LN were extirpated under sterile conditions, rinsed thoroughly in RPMI medium, minced into small sections with sterile scissors and pressed through sterile stainless steel mesh. Cells were washed twice in RPMI medium, minced into small sections with sterile scissors and pressed through sterile stainless steel mesh. Cells were washed twice in RPMI medium and lymphocytes were separated by Ficoll-Hypaque gradient centrifugation.

6.1.4. Monoclonal Antibodies

The following mAbs specific for TCR V gene segments were tested:

| Specificity | mAb | Reference |
| --- | --- | --- |
| $V_\beta 5.1$ | LC4 | Maecker et al., J. Immunol. 142: 1395 (1989) |
| $V_\beta 5.2 + 5.3$ | 1Cl | Boylston et al., J. Immunol. 137: 741 (1989) |
| $V_\beta 5.3$ | W112 | Tian et al., Proc. J. 3:A486 (1989) |
| $V_\beta 6.7$ | OT145 | Posnett et al., Proc. Natl. Acad. Sci. 83:7888 (1986) |
| $V_\beta 8$ | 16G8 | Tian et al., supra |
| $V_\beta 12$ | S511 | Bigler et al., J. Exp. Med. 158: 1000 (1983) |
| $V_\alpha 12.1$ | 6D6 | DerSimonian et al., J. Exp. Med. 174:639 (1991) |
| $V_\alpha 2.3$ | F1 | Janson et al., Cancer Immunol. Immunother 28:225 (1989), produced in the present inventors' lab |

The reactivities of these mAb may include more V gene members than indicated above.

The OKT3 (anti-CD3) hybridoma was acquired from American Type Culture Collection (Rockville, Md.). Phycoerythrin (PE)-conjugated mAbs Leu-3a (anti-CD4), IL2R (anti-CD25), HLA-DR and Leu-18 (anti CD45) were obtained from Becton Dickinson (Mountain View, Calif.).

The mAb 4B4 (anti-CD29) was purchased from Coulter Corporation, Inc. (Hialeah, Fla.).

The TCR δ1 mAb (T Cell Sciences Inc.) was used as a marker for the γ/δ TCR.

FITC-conjugated F(ab')$_2$ fragments of rabbit anti-mouse Ig were obtained from Dakopatts A/S (Glostrup, Denmark). Normal mouse serum (NMS, produced from BALB/c mice, was used for negative control at a dilution of 1:500 in PBS.

6.1.5. Flow Cytometric Analysis

Cells were incubated for 30 min with unlabeled TCR-specific mAb or NMS, washed twice with PBS and incubated with FITC-conjugated F(ab')$_2$ fragments of rabbit anti-mouse Ig for 30 min. The cells were washed three times with PBS. NMS, diluted 1:500, was thereafter added to block remaining rabbit anti-mouse Ig. After 10 min., PE-conjugated mAb was added, the cells were incubated for 20 min and washed twice in PBS. Ten thousand cells were analyzed in a FACScan® flow cytometer (Becton Dickinson) and a Hewlett Packard 300 computer (Palo Alto, Calif.). Lymphocytes were gated out by forward and side scatter, and dead cells by staining with propidium iodide. NMS, used as negative control always stained ≦0.5% of the cell population. Optimal compensation was set for green and orange fluorescence.

6.1.6. Definition of T Cell Subpopulations

The CD4$^+$ T subpopulation was defined as those cells which were Leu-3$^+$, OKT3$^+$, and TcRδ1$^-$. An abnormal compartmentalization was characterized as more than >10% CD4$^+$ T in BAL occurring together with a more than 3-fold increased reactivity for a particular TCR-specific mAb in BAL as compared to PBL

6.1.7. HLA Typing

HLA class I antigens (A, B and C) and DR antigens were determined by the microlymphocytotoxicity technique well-known in the art using antisera which were available locally or commercially. Genomic HLA-DR and HLA-DQ typing was performed using TaqI RFLP analysis (Carlsson, B. et al., supra).

6.1.8. Statistical Analysis

The differential counts of alveolar cells and the percentages of cells positive in a reaction with a given mAb are presented as the medians with i.q.r. The p values were obtained by the use of the non-parametric Wilcoxon-Mann-Whitney two-tailed test.

6.2. Results

6.2.1. Characterization of T Lymphocytes from PBL and BAL

In line with earlier findings, the present study showed an accumulation of Th cells ($CD4^+$) in the alveolar space of sarcoidosis patients (Table 1). The median percentage of $CD4^+$ T cells in the total T cell population was 84% in BAL versus 57% in PBL.

The accumulated BAL $CD3^+$ cells showed signs of activation, unlike the PBL T cells. Thus, 40% of the $CD3^+$ cells in BAL expressed HLA-DR, compared to 5.4% in PBL. The expression of CD25 did not show such a difference: 3.0% of $CD3^+$ BAL cells were $CD25^+$ and 2.6% of $CD3^+$ PBL were $CD25^+$.

The CD29 molecule is expressed by memory cells (Sanders, M. E. et al., *J. Immunol.* 140:1401 (1988)), and the $CD4^+$ T cells which are also $CD29^+$ have been defined as a "helper inducer" subset (Morimoto, C. et al., *J. Immunol.* 134:3762 (1985)). The median percentage of $CD29^+$ cells in the $CD4^+$ BAL cell population was 96%. In contrast, only 51% of $CD4^+$ PBL were $CD29^+$.

The mAb Leu-18 (CD45RA) defines the "suppressor inducer" subset of T cells (Morimoto, C. et al., *J. Immunol.* 134:1508 (1985)) which includes "virgin" cells (Kristensson, K. et al., *Scand. J. Imunol.* 32:243 (1990)). The expression of $CD45RA^+$ cells in sarcoidosis patients also markedly differed between the two compartments: about 1% of $CD4^+$ BAL cells were $CD45RA^+$ in contrast to 43% of $CD4^+$ PBLs.

TABLE 1

Characterization of PBL and BAL T Cells
from Sarcoidosis Patients nos. 1–11[a]

| Subset | PBL | BAL |
|---|---|---|
| $\gamma\delta^+/CD3^+$ | 6.7 (4.2–12.5) | 1.8 (1.0–2.4) |
| $IL2R^+/CD3^+$ | 2.6 (1.9–5.0) | 3.0 (2.4–4.6) |
| $HLA\text{-}DR^+/CD3^+$ | 5.4 (4.3–5.8) | <u>40.0</u> (22–49) |
| $CD4^+/CD3^+$ | 57.1 (47–73) | <u>83.8</u> (70–87) |
| $CD29^+/CD4^{+b}$ | 51.0 (28–73) | <u>96.0</u>(93–98) |
| $CD45RA^+/CD4^{+c}$ | 43.0 (36–55) | <u>0.6</u> (0.4–1.0) |

[a]Bold figures show the median reactivity, as percent of $CD3^+$ or $CD4^+$ cells within PBL and BAL. Underlined values are abnormal. Figures in parentheses show the i.q.r. (P25–P75).
[b]Normal value is 41% (Morimoto et al., J. Immunol. 134:3762 (1985)).
[c]Normal values are 41% (Morimoto et al., J. Immunol. 134:1508 (1985)).

6.2.2. TCR V Gene Expression in $CD4^+$ Cells

Figure 1A:
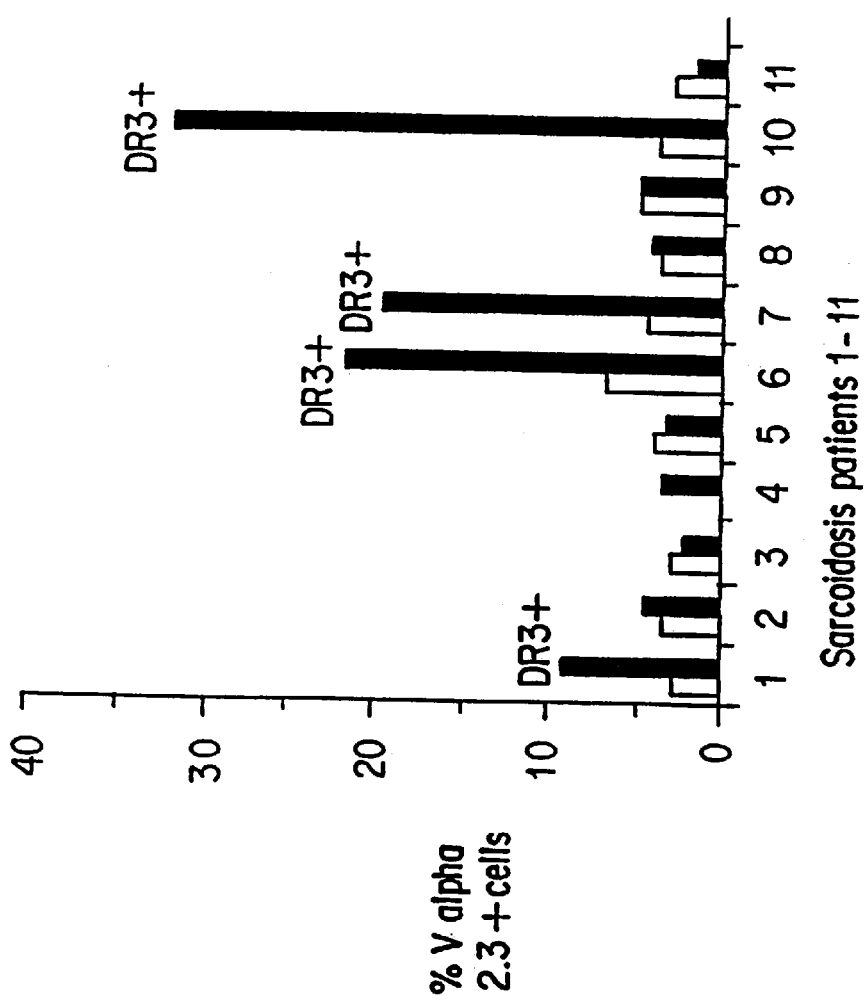

The reactivity of the TCR-specific mAbs with BAL cells and PBL were compared. In 27% (3/11) of the sarcoidosis patients, distinct signs of compartmentalization of $CD4^+$ T lymphocytes in the lung were evident (FIG. 1, Table 2).

Figure 2C:
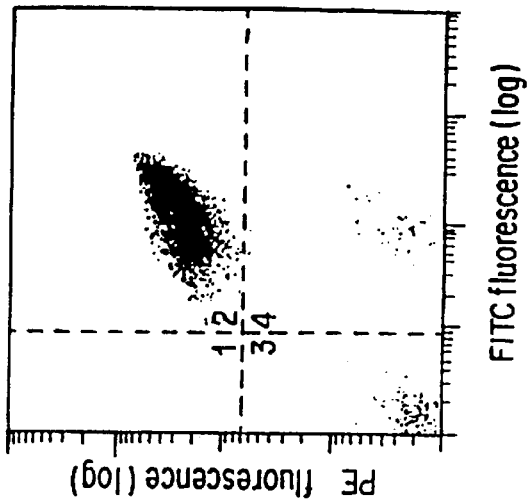
Figure 2B:
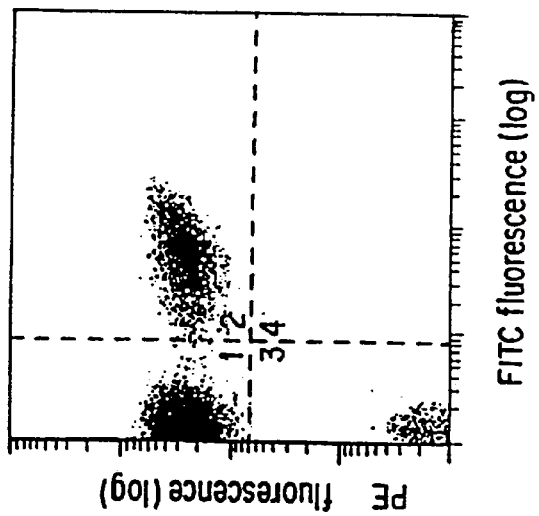
Figure 2A:
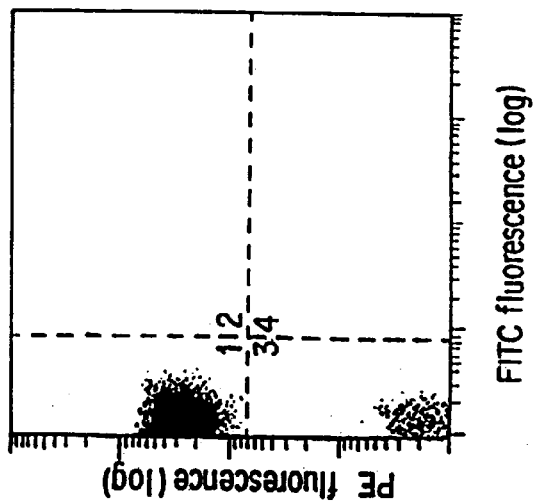

In all three of these patients, the localized $CD4^+$ BAL T cells were reactive with the $V_\alpha 2.3$-specific mAb. In patient no. 10, 31.9% of the $CD4^+$ BAL cells were $V_\alpha 2.3^+$ (FIG. 2), compared to 3.8% in PBL. In patients nos. 6 and 7, 21.7% and 19.6%, respectively, of BAL $CD4^+$ T cells were $V_\alpha 2.3^+$ and 6.8% and 4.5%, respectively, of $CD4^+$ PBL were $V_\alpha 2.3^+$. Additionally, patient no. 1 showed an accumulation of $V_\alpha 2.3^+$ cells among $CD4^+$ T cells in the lung, with a more than 3-fold increase in percentage (9.0%) compared to PBL (2.8%).

In the initial study, no correlation was observed between the distribution of $V_\alpha 2.3^+ CD4^+$ T cells in the lung and active vs. inactive disease, acute vs. non-acute disease, or chest radiography. However, subsequent analyses of larger number of patients showed a relationship between lung localization and sarcoidosis (see below). No other such lung compartmentalization was observed in cells reacting with any of the other TCR α-specific mAbs (Table 2).

The four patients showing compartmentalization of $V_\alpha 2.3^+ CD4^+$ T cells to the lung (No's. 1, 6, 7 and 10) were subjected to an additional round of reanalysis (Table 3, FIG. 3) 6 months, or later, after the initial test. During this period, patients nos. 1 and 10 appeared to have been clinically cured, either spontaneously (No. 10) or by steroid-treatment (No. 1). Patients No. 6 and 7 did not present with any subjective symptoms at the time of initial investigation, and patient No. 7 appeared well at the time of the first and second analysis.

At the time of reanalysis, Patient No. 6 had symptoms of active sarcoidosis disease including coughing, fever and enlarged cervical LN.

Figure 3:
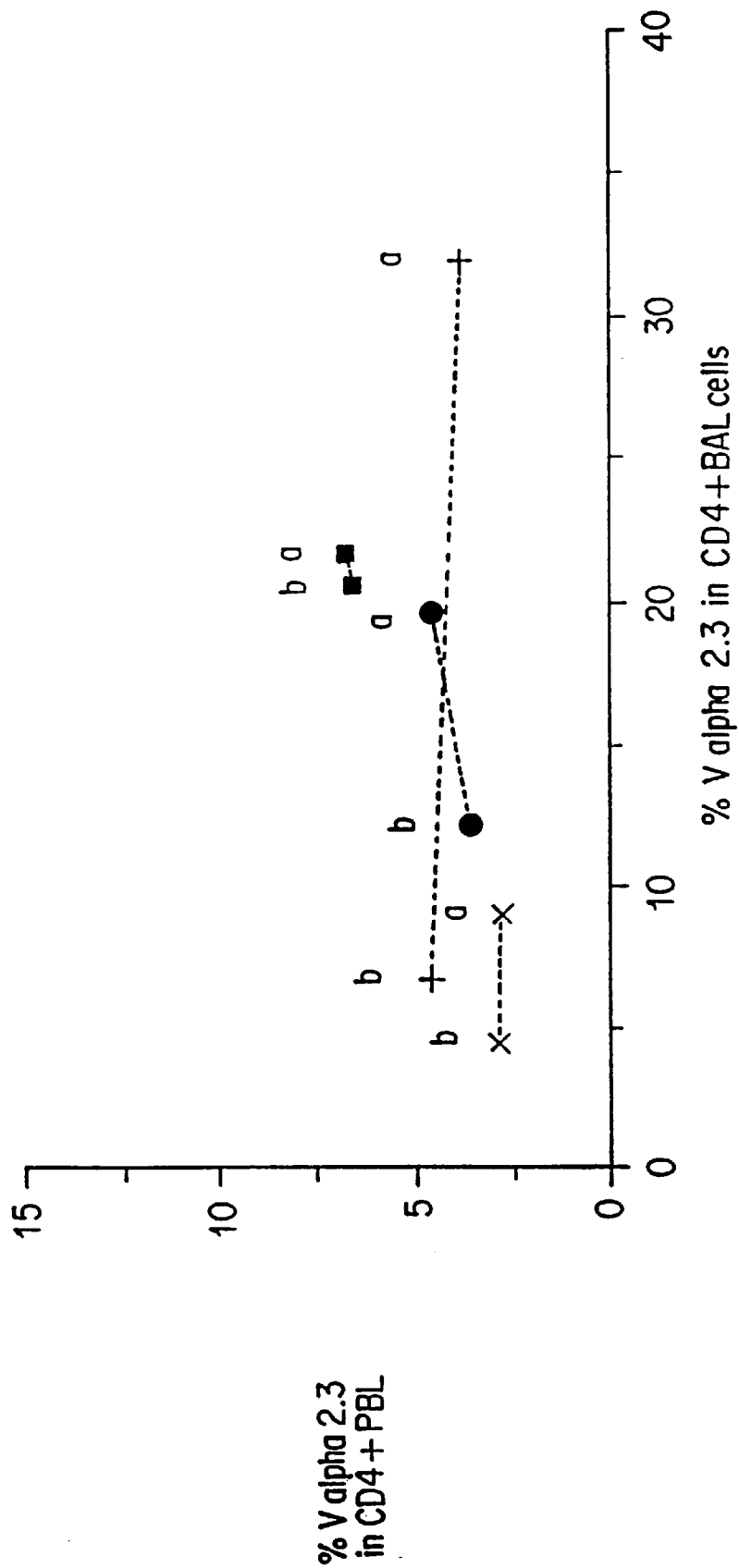

As can be seen in FIG. 3 and Table 3, after cure, patients No. 1 and 10 had normalized values of $V_\alpha 2.3^+ CD4^+$ T cells in BAL, while displaying virtually the same normal frequencies of $V_\alpha 2.3^+ CD4^+$ T cells in PBL.

In contrast, patient no. 6, in particular, but also patient no. 7, maintained the abnormal compartmentalization of such T cells in BAL.1

TABLE 2

Percent of CD4+ BAL Lymphocytes or CD4+ PBL Reactive with TCR Specific mAb in Sarcoidosis Patients (1–11) and Healthy Controls (A–D)

| | TCR-specific mAb | | | | | | | |
|---|---|---|---|---|---|---|---|---|
| Subject | $V_\alpha 2.3$ | $V_\alpha 12.1$ | $V_\beta 5.1$ | $V_\beta 5.2 + 5.3$ | $V_\beta 5.3$ | $V_\beta 6.7$ | $V_\beta 8$ | $V_\beta 12$ |
| 1 | 9.0/2.8 | 0.9/4.4 | 4.0/4.4 | 3.4/2.3 | 1.3/0.8 | 5.6/9.8 | 6.7/3.6 | 1.7/1.1 |
| 2 | 4.5/3.3 | 3.4/3.4 | 4.5/5.9 | 3.4/3.0 | 1.9/1.0 | 6.1/3.6 | 3.2/5.8 | 2.0/2.1 |
| 3 | 2.0/2.9 | 2.1/4.4 | 4.7/4.9 | 2.6/2.8 | 0.8/1.2 | 5.1/3.7 | 3.0/3.3 | 1.0/1.6 |
| 4 | 3.4/ND | 3.1/ND | 10.2/ND | 1.4/ND | 0.9/ND | 3.7/ND | 3.2/ND | 1.2/ND |
| 5 | 3.0/3.9 | 1.3/3.1 | 6.3/5.3 | 3.4/3.0 | 2.2/1.0 | 7.1/5.9 | 7.9/5.6 | 1.3/1.4 |
| 6 | <u>21.7/6.8</u>[a] | 1.5/2.2 | 4.6/5.6 | 5.3/2.9 | 2.0/1.3 | 8.2/5.5 | 3.3/2.9 | 3.0/1.9 |
| 7 | <u>19.6/4.5</u> | 1.6/2.3 | 4.4/4.9 | 2.1/2.5 | 0.8/0.9 | 6.5/3.8 | 2.8/4.2 | 0.7/1.1 |
| 8 | 4.1/3.5 | 3.3/3.3 | 2.8/4.7 | 3.9/2.1 | 2.6/0.6 | 4.0/3.5 | 4.9/4.0 | 1.5/1.5 |
| 9 | 4.8/4.8 | 2.4/2.8 | 3.5/4.6 | 3.5/2.1 | 1.6/1.2 | 5.1/3.6 | 5.2/9.1 | 0.8/2.5 |
| 10 | <u>31.9/3.8</u> | 0.8/2.8 | 5.7/6.3 | 4.0/2.1 | 2.2/1.0 | 6.8/6.7 | 5.8/4.3 | 1.9/2.1 |
| 11 | 1.8/3.2 | 3.6/2.4 | 5.1/4.0 | 3.5/3.4 | 1.3/1.4 | 4.7/3.7 | 8.2/4.5 | 2.1/1.8 |
| A[b] | 6.0/3.3 | 3.1/3.1 | 3.3/3.5 | 3.7/2.0 | 0.8/0.9 | 6.2/3.3 | 3.1/4.2 | 4.4/2.0 |
| B | 3.0/4.1 | ND/ND | 3.7/3.7 | 1.8/2.2 | 0.5/0.9 | 6.8/4.3 | 9.1/4.1 | 8.4/1.6 |
| C | 7.6/5.1 | 1.4/1.7 | 7.6/7.4 | 5.5/2.5 | ND/ND | 1.4/2.3 | 3.9/4.6 | 2.4/2.0 |
| D | 7.8/2.7 | ND/1.6 | ND/5.4 | ND/3.1 | ND/0.8 | ND/5.2 | ND/4.9 | ND/2.0 |

[a]Underlined figures in table show signs of compartmentalization of TCR+ cells (i.e. greater than three times the value of percentage in BAL compared to PBL, plus >10% reactivity in BAL) to the lung.
[b]A–D are healthy controls. A and B are HLA-DR3−; C and D are HLA-DR3+.

TABLE 3

Second Analysis of Sarcoidosis Patient Lymphocyte Reactivity with Anti-TcR mAb

| | Anti-TcR mAb | | | | | | |
|---|---|---|---|---|---|---|---|
| Patients | $V_\alpha 2.3$ | $V_\alpha 12.1$ | $V_\beta 5.1$ | $V_\beta 5.2 + 5.3$ | $V_\beta 6.7$ | $V_\beta 8$ | $V_\beta 12$ |
| 1 | 4.5/2.9[1] | ND/3.9 | ND/3.4 | ND/2.5 | ND/6.7 | 6.3/2.6 | ND/1.2 |
| 6 | <u>20.6/6.6</u>[2] | 1.3/2.4 | 3.8/4.9 | 5.5/3.8 | 9.7/4.9 | 2.9/3.3 | 2.8/2.6 |
| 7 | <u>12.2/3.6</u> | ND/2.1 | ND/5.3 | ND/3.8 | ND/3.8 | ND/4.2 | ND/1.6 |
| 10 | 6.8/4.6 | 1.8/2.8 | 3.5/4.5 | 8.3/5.6 | 8.3/5.6 | 2.9/4.4 | 1.5/2.5 |
| 6/LN[3] | 7.0 | 2.8 | 4.6 | 3.0 | 7.0 | 4.1 | 2.3 |

[1]% of CD4+ BAL/% of CD4+ PBL reactive with mAb
[2]Underlined figures show signs of compartmentalization of TCR+ cells.
[3]6/LN represents cervical lymph node lymphocytes from patient 6.

Analysis of total cell and lymphocyte counts in BAL in these four patients revealed a decrease in the total number of lymphocytes in patients No. 1 and 10, in contrast to patients No. 6 and 7 (Table 4). In addition, the number of CD3+CD4+ cells was reduced in BAL, but not in PBL, in patients 1 and 10, as compared to patients 6 and 7 who still had high percentages of CD3+CD4+ cells in BAL (Table 5).

Patient 6 presented with enlarged cervical LN at the time of the second analysis. One such LN was extirpated and analyzed for TCR V gene usage. Interestingly, the percent of cells expressing the $V_\alpha 2.3$ gene was similar in the LN (7.0%) and the PBL (6.6%) populations (Table 3).

TABLE 4

Total Cell and Lymphocyte Counts in BAL of Sarcoidosis Patients at Time of Disease Onset (First Analysis) and More than 6 Months Later (Second Analysis)

| | First analysis | | Second analysis | |
|---|---|---|---|---|
| Patient | TCC[a] | LC[b] | TCC | LC |
| 1 | 144 | 25 (18%)[c] | 84 | 11 (14%) |
| 6 | 125 | 28 (22%) | 95 | 33 (34%) |
| 7 | 60 | 5 (9%) | 94 | 9 (9%) |
| 10 | 152 | 61 (40%) | 101 | 5 (5%) |

[a]TCC = Total cell count ($\times 10^6$/l).
[b]LC = Lymphocyte count ($\times 10^6$/l).
[c]Numbers in parentheses are the percentage of lymphocytes in the total cell count.

TABLE 5

Percentages of CD3+ and CD4+ BAL Lymphocytes in Sarcoidosis Patients at Time of Disease Onset (First Analysis) and More than 6 Months Later (Second Analysis)

| Patient | First analysis | | Second analysis | |
|---|---|---|---|---|
| | % CD3+ | % CD4+ | % CD3+ | % CD4+ |
| 1 | 72 | 46 | 22 | 15 |
| 6 | 82 | 74 | 88 | 82 |
| 7 | 50 | 35 | 89 | 62 |
| 10 | 97 | 93 | 92 | 64 |

6.2.3. HLA Typing

Since the TCR recognize antigen in the context of MHC, it was important to define the HLA phenotypes of the patients, to understand the possible relation between selective TCR usage in compartmentalized T cells of sarcoidosis patients with MHC antigen expression in these cell populations. Thus, patients and controls were HLA typed (Table 6).

Interestingly, the three patients with highly significant compartmentalization of $V_\alpha 2.3^+CD4^+$ T cells in BAL (No. 6, 7 and 10) were all HLA-B8, Cw7, DR3(w17), DQw2+. DRw17 is a recently introduced split of DR3. A fourth patient (no. 1) with a moderate accumulation of $V_\alpha 2.3^+$ CD4+ T cells in BAL also expressed the HLA-DR3(w17), DQw2 haplotype.

haplotype and the BAL/PBL, ratio of cells expressing any other TCR chain based on reactivity with other anti-TCR mAbs.

6.2.4. Controls

No compartmentalization of any of the TCR mAb-reactive cells was detected in any of four healthy controls (Table 2). Two of these individuals were HLA-DR3+.

6.2.5. Analysis of Additional Patients

Studies performed subsequent to those described above analyzed the CD4+ T lymphocytes in BAL and PBL of sarcoidosis patients that were either of the HLA-DR3(w17) type (designated DR3+) or were of other HLA-DR types (designated DR3−). A total of 27 patients (inclusive of those described above) were studied, 12 DR3+ and 15 DR3−. The results of expression of TCR α or β chains in the PBL or BAL of these patients, or of controls, compared by HLA-DR type or by PBL vs. BAL, are summarized in Tables 7–11 below.

TABLE 7

PERCENTAGE OF CD4+ T LYMPHOCYTES EXPRESSING VARIOUS TCR α or β CHAINS IN SARCOIDOSIS PATIENTS (n = 27)

| | LYMPHOCYTES FROM: | | |
|---|---|---|---|
| TCR | Bronchoalveolar Lavage | Peripheral Blood | p-value |
| Vα2.3 | 4.5 (3.4–14.8) | 3.4 (3.0–4.3) | 0.015* |
| Vα12.1 | 1.6 (1.1–2.4) | 2.7 (2.2–3.3) | 0.001* |

TABLE 6

HLA Haplotypes of Sarcoidosis Patients and Healthy Controls

| | HLA- | | | | |
|---|---|---|---|---|---|
| Patient | A | B | C | DR | DQ |
| 1[a] | A2 | B7,15 | Cw3,w7? | DR2(w15), 3(w17)[b] | DQw1(w6),w2 |
| 2 | A2,3 | B7,15 | Cw3,w7 | DR2(w15),4 | DQW1(w6),w3(w8) |
| 3 | A2,3 | B7,18 | Cw7 | DR2(w15),5(w11) | DQw1(w6),w3(w7) |
| 4 | A9(24),11 | B5,12(44) | Cw8? | DR4,7 | DQw2,w3(w8) |
| 5 | A2 | B5,13 | Cw2?,w5?,w6? | DR2(w15), 5(w11) | DQw1(w6),w3(w7) |
| 6 | A3,w19(31) | B7,8 | CW7 | DR2(w15), 3(w17) | DQw1(w6),w2 |
| 7 | A1,11 | B8,27 | Cw2,w7? | DR3(w17),4 | DQw2, w3(w8) |
| 8 | A3,w19(32) | B12,27 | Cw1,w5 | DR1,2(w15) | DQw1(w5),w1(w6) |
| 9 | A9(24) | B5,40 | Cw3? | DR2(w15),4 | DQw1(w6),w3(w8) |
| 10 | A1, w19(29) | B8,12w | Cw6,w7 | DR3(w17),4 | DQw2,w3(w7) |
| 11 | ND[c] | ND | ND | DRw6,w14 | DQw1,ws |
| Control[d] | | | | | |
| A | A2 | B12(44) | Cw5 | DR1, 2 | ND |
| B | ND | ND | ND | DR2(w16),7 | DQw3(w7),w3(w9) |
| C | A1, 3 | B8,27 | Cw2,w7? | DR1,3 | ND |
| D | A1, 2 | B8,27 | Cw2,w7? | DR2,3 | ND |

[a]Patients whose identification numbers are underlined show compartmentalization or accumulation of $V_\alpha 2.3^+CD4^+$ cells in the lung.
[b]Underlined HLA types are HLA-DR3(w17) and/or DQW/2 haplotypes.
[c]ND = not determined
[d]A–D refer to healthy controls. A and B are HLA-DR3−, C and D are HLA-DR3+.

In contrast, all remaining patients were DR3(w17), DQw2−.

The positive correlation found between expression of the HLA-DR3(w17), DQw2 haplotype and the ratio of $V_\alpha 2.3$ positivity between CD4+ BAL and CD4+ PBL was highly significant (p<0.002). No statistically significant correlations were observed between the HLA-DR3(w17), DQw2

TABLE 7-continued

PERCENTAGE OF CD4+ T LYMPHOCYTES EXPRESSING VARIOUS TCR α or β CHAINS IN SARCOIDOSIS PATIENTS (n = 27)

| TCR | LYMPHOCYTES FROM: Bronchoalveolar Lavage | Peripheral Blood | p-value |
|---|---|---|---|
| Vβ2 | 11.0 (7.4–13.8) | 9.8 (9.0–11.1) | — |
| Vβ3 | 2.7 (1.4–5.0) | 5.2 (1.6–5.4) | — |
| Vβ5.1 | 4.6 (3.6–5.7) | 4.9 (4.6–6.1) | 0.242 |
| Vβ6 | 5.1 (3.6–6.3) | 3.8 (3.4–5.0) | 0.226 |
| Vβ8 | 4.1 (3.1–5.5) | 4.4 (3.8–5.5) | 0.516 |
| Vβ12 | 1.9 (1.2–2.5) | 1.8 (1.4–2.1) | 0.582 |

Results represent the median and confidence interval (10%–90% of the percentage of cells staining as positive with mAbs which characterize the denoted TCR chain.
*statistically significant difference between BAL lymphocytes and PRL (Student's t test)

TABLE 8

PERCENTAGE OF CD4+ T LYMPHOCYTES EXPRESSING VARIOUS TCR α or β CHAINS IN HLA-DR3-POSITIVE SARCOIDOSIS PATIENTS (n = 12)

| TCR | LYMPHOCYTES FROM: Bronchoalveolar Lavage | Peripheral Blood | p-value |
|---|---|---|---|
| Vα2.3 | 17.5 (11.9–27.4) | 4.1 (3.6–5.2) | <0.001* |
| Vα12.1 | 0.9 (0.8–1.7) | 2.4 (2.1–2.9) | <0.001* |
| Vβ2 | 8.4 | 10.7 (9.4–13.4) | — |
| Vβ3 | 5.9 | 3.7 (1.7–5.4) | — |
| Vβ5.1 | 4.6 (4.2–5.7) | 6.0 (5.1–6.4) | 0.159 |
| Vβ6 | 5.6 (2.8–6.7) | 4.1 (3.9–5.3) | 0.390 |
| Vβ8 | 3.9 (3.1–5.3) | 4.3 (4.1–4.7) | 0.435 |
| Vβ12 | 2.3 (1.8–3.8) | 1.9 (1.2–2.0) | 0.121 |

Results represent the median and confidence interval (10%–90% of the percentage of cells staining as positive with mAbs which characterize the denoted TCR chain.
*statistically significant difference between BAL lymphocytes and PRL (Student's t test)

TABLE 9

PERCENTAGE OF CD4+ T LYMPHOCYTES EXPRESSING VARIOUS TCR α or β CHAINS IN HLA-DR3-NEGATIVE SARCOIDOSIS PATIENTS (n = 15)

| TCR | LYMPHOCYTES FROM: Bronchoalveolar Lavage | Peripheral Blood | p-value |
|---|---|---|---|
| Vα2.3 | 3.5 (2.6–4.1) | 3.1 (2.7–3.3) | 0.303 |
| Vα12.1 | 2.1 (1.4–3.2) | 3.0 (2.4–3.4) | 0.075 |
| Vβ2 | 12.9 (9.2–15.5) | 9.1 (7.8–9.7) | — |
| Vβ3 | 2.7 (1.1–3.2) | 5.2 (1.9–5.3) | — |
| Vβ5.1 | 4.6 (3.0–5.8) | 4.8 (4.3–5.3) | 0.697 |
| Vβ6 | 4.5 (3.6–5.6) | 3.6 (3.1–3.8) | 0.226 |
| Vβ8 | 4.5 (3.1–5.4) | 4.6 (3.4–5.7) | 0.645 |
| Vβ12 | 1.4 (1.1–2.2) | 1.7 (1.4–2.2) | 0.472 |

Results represent the median and confidence interval (10%–90% of the percentage of cells staining as positive with mAbs which characterize the denoted TCR chain.
*statistically significant difference between BAL lymphocytes and PRL (Student's t test)

TABLE 10

COMPARISON OF CD4+ T LYMPHOCYTES EXPRESSING VARIOUS TCR α or β CHAINS IN BRONCHOALVEOLAR LAVAGE FLUID LYMPHOCYTES IN HLA-DR3-POSITIVE VERSUS HLA-DR3-NEGATIVE SARCOIDOSIS PATIENTS

| TCR | HLA-DR3+ (n = 12) | HLA-DR3− (n = 15) | p-value |
|---|---|---|---|
| Vα2.3 | 17.5 (11.9–27.4) | 3.5 (2.6–4.1) | <0.001* |
| Vα12.1 | 0.9 (0.8–4.7) | 2.1 (1.4–3.2) | 0.013* |
| Vβ2 | 8.4 | 12.9 (9.2–15.5) | — |
| Vβ3 | 5.9 | 2.7 (1.1–3.2) | — |
| Vβ5.1 | 4.6 (4.2–5.7) | 4.6 (3.0–5.8) | 0.555 |
| Vβ6 | 5.6 (2.8–6.7) | 4.5 (3.6–5.6) | 0.238 |
| Vβ8 | 3.9 (3.1–5.3) | 4.5 (3.1–5.4) | 0.818 |
| Vβ12 | 2.3 (1.8–3.8) | 1.4 (1.1–2.2) | 0.150 |

Results represent the median and confidence interval (10%–90% of the percentage of cells staining as positive with mAbs which characterize the denoted TCR chain.
*statistically significant difference between BAL lymphocytes from DR3+ patients (n = 12) versus DR3− patient (n = 15) (Student's t test)

TABLE 11

COMPARISON OF CD4+ T LYMPHOCYTES EXPRESSING VARIOUS TCR α or β CHAINS IN PERIPHERAL BLOOD OF HLA-DR3-POSITIVE VERSUS HLA-DR3-NEGATIVE SARCOIDOSIS PATIENTS

| TCR | HLA-DR3+ (n = 12) | HLA-DR3− (n = 15) | p-value |
|---|---|---|---|
| Vα2.3 | 4.1 (3.6–5.2) | 3.1 (2.7–3.3) | 0.004* |
| Vα12.1 | 2.4 (2.1-2.9) | 3.0 (2.4-3.4) | 0.134 |
| Vβ2 | 10.7 (9.4-13.4) | 9.1 (7.8-9.7) | |
| Vβ3 | 3.7 (1.7-5.4) | 5.2 (1.9-5.3) | |
| Vβ5.1 | 6.0 (5.1-6.4) | 4.8 (4.3-5.3) | 0.020* |
| Vβ6 | 4.1 (3.9-5.3) | 3.6 (3.1-3.8) | 0.075 |
| Vβ8 | 4.3 (4.1-4.7) | 4.6 (3.4-5.7) | 0.803 |
| Vβ12 | 1.9 (1.2-2.0) | 1.7 (1.4-2.2) | 0.741 |

Results represent the median and confidence interval (10%–90% of the percentage of cells staining as positive with mAbs which characterize the denoted TCR chain.
*statistically significant difference between PBL from DR3+ patients (n = 12) versus DR3− patient (n = 15) (Student's t test)

6.3. Discussion

The HLA-DR3(w17) antigen, expressed by 17.2% of the Swedish population, is associated with autoimmune diseases such as SLE, juvenile diabetes, Graves'disease and celiac disease (Tiwari, J. et al., *HLA and Disease Association* (1985)). Thus, in a subgroup of sarcoidosis patients, the present inventors have identified two of the structures in the specific trimolecular complex constituted by the TCR, MHC and antigen. This finding suggests the presence of a specific antigen being responsible for the pulmonary disease in sarcoidosis patients, here expressed as $V_\alpha 2.3^+CD4^+$ TCR linked to the HLA-DR3(w17), DQW2 haplotype.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains.

7. Deposits

One illustrative hybridoma cell line designated TM 19 MCB secreting monoclonal antibody F1 was deposited on Nov. 4, 1992, at the American Type Culture Collection, 10801 University Boulevard, Manassas, Va., 20110-2209, and was given accession number ATCC #HB 11176.

The methods and compositions of the present invention are not intended to be limited to this cell line or its monoclonal antibody products.

What is claimed is:

1. A method of treating sarcoidosis in a subject, comprising administering to the subject an amount effective for treatment of sarcoidosis of a monoclonal antibody specific for an epitope of the variable region of the T cell receptor $V_\alpha 2.3$ chain, or an antigen-binding fragment or derivative of the monoclonal antibody.

2. A method according to claim 1 wherein the monoclonal antibody, fragment, or derivative is linked to a pharmacologic agent.

3. A method according to claim 1, wherein the monoclonal antibody is F1, as produced by the hybridoma deposited with the ATCC and assigned accession number HB 11176.

* * * * *